United States Patent
Mixter et al.

(10) Patent No.: US 11,058,581 B2
(45) Date of Patent: Jul. 13, 2021

(54) ADJUSTABLE FLOW GLAUCOMA SHUNTS AND METHODS FOR MAKING AND USING SAME

(71) Applicant: Shifamed Holdings, LLC, Campbell, CA (US)

(72) Inventors: Colin Mixter, Campbell, CA (US); Claudio Argento, Felton, CA (US); Andrew Backus, Campbell, CA (US); Tom Saul, Moss Beach, CA (US)

(73) Assignee: Shifamed Holdings, LLC, Campbell, CA (US)

( * ) Notice: Subject to any disclaimer, the term of this patent is extended or adjusted under 35 U.S.C. 154(b) by 0 days.

(21) Appl. No.: 16/632,008

(22) PCT Filed: Jul. 20, 2018

(86) PCT No.: PCT/US2018/043158
§ 371 (c)(1),
(2) Date: Jan. 17, 2020

(87) PCT Pub. No.: WO2019/018807
PCT Pub. Date: Jan. 24, 2019

(65) Prior Publication Data
US 2020/0229977 A1    Jul. 23, 2020

Related U.S. Application Data

(60) Provisional application No. 62/535,125, filed on Jul. 20, 2017, provisional application No. 62/626,615, (Continued)

(51) Int. Cl.
*A61F 9/007* (2006.01)
*A61F 9/00* (2006.01)
(Continued)

(52) U.S. Cl.
CPC ........ *A61F 9/00781* (2013.01); *A61F 9/0017* (2013.01); *A61M 27/002* (2013.01);
(Continued)

(58) Field of Classification Search
CPC ........ A61F 9/00781; A61F 2210/0014; A61M 27/002
See application file for complete search history.

(56) References Cited

U.S. PATENT DOCUMENTS

| | | |
|---|---|---|
| 5,070,697 A | 12/1991 | Van Zeggeren |
| 5,123,906 A | 6/1992 | Kelman |

(Continued)

FOREIGN PATENT DOCUMENTS

| | | |
|---|---|---|
| AU | 2014201621 B2 | 3/2016 |
| AU | 2016201445 B2 | 3/2016 |

(Continued)

OTHER PUBLICATIONS

International Search Report and Written Opinion received for PCT Application No. PCT/US18/43158, filed Jul. 20, 2018, Applicant: Shifamed Holdings, LLC, dated Nov. 23, 2018, 12 pages.

(Continued)

*Primary Examiner* — Leslie R Deak
(74) *Attorney, Agent, or Firm* — Perkins Coie LLP

(57) ABSTRACT

Adjustable flow glaucoma shunts are disclosed herein. In one embodiment, for example, an adjustable flow shunt can include an outflow drainage tube having a proximal inflow region and a distal outflow region. The proximal inflow region can include aperture(s) defining a fluid inlet area positioned to allow fluid to flow therethrough. The shunt further comprises an inflow control assembly at the proximal inflow region. The inflow control assembly can include a control element configured to slidably engage the proximal inflow region and a spring element. The spring element is (Continued)

configured to be activated by non-invasive energy and, upon activation, slidably move the control element along the proximal inflow region such that (a) the one or more apertures are accessible and have a first fluid flow cross-section or (b) the one or more apertures are at least partially covered by the control element and have a second, different fluid-flow cross-section.

20 Claims, 16 Drawing Sheets

Related U.S. Application Data filed on Feb. 5, 2018, provisional application No. 62/643,125, filed on Mar. 14, 2018.

(51) Int. Cl.
  *A61M 27/00* (2006.01)
  *A61F 9/008* (2006.01)

(52) U.S. Cl.
  CPC ............ *A61F 2009/00891* (2013.01); *A61F 2210/0014* (2013.01); *A61F 2250/0001* (2013.01); *A61M 2210/0612* (2013.01)

(56) References Cited

U.S. PATENT DOCUMENTS

| | | | |
|---|---|---|---|
| 5,891,111 A * | 4/1999 | Ismael | A61M 25/003 604/541 |
| 6,077,299 A | 6/2000 | Adelberg et al. | |
| 6,261,256 B1 | 7/2001 | Ahmed | |
| 6,450,984 B1 | 9/2002 | Lynch et al. | |
| 6,508,779 B1 | 1/2003 | Suson | |
| 6,626,858 B2 | 9/2003 | Lynch et al. | |
| 6,638,239 B1 | 10/2003 | Bergheim et al. | |
| 6,666,841 B2 | 12/2003 | Gharib et al. | |
| 6,736,791 B1 | 5/2004 | Tu et al. | |
| 7,025,740 B2 | 4/2006 | Ahmed | |
| 7,207,965 B2 | 4/2007 | Simon | |
| 7,458,953 B2 | 12/2008 | Peyman | |
| 7,699,882 B2 * | 4/2010 | Stamper | A61F 9/00781 623/1.11 |
| 7,717,872 B2 | 5/2010 | Shetty | |
| 7,947,008 B2 | 5/2011 | Grahn et al. | |
| 8,012,134 B2 | 9/2011 | Claude et al. | |
| 8,298,240 B2 | 10/2012 | Giger et al. | |
| 8,308,701 B2 | 11/2012 | Horvath et al. | |
| 8,506,515 B2 | 8/2013 | Burns et al. | |
| 8,540,659 B2 | 9/2013 | Berlin | |
| 8,585,629 B2 | 11/2013 | Grabner et al. | |
| 8,663,303 B2 | 3/2014 | Horvath et al. | |
| 8,721,702 B2 | 5/2014 | Romoda et al. | |
| 8,758,290 B2 | 6/2014 | Horvath et al. | |
| 8,765,210 B2 | 7/2014 | Romoda et al. | |
| 8,771,220 B2 | 7/2014 | Nissan et al. | |
| 8,801,766 B2 | 8/2014 | Reitsamer et al. | |
| 8,828,070 B2 | 9/2014 | Romoda et al. | |
| 8,852,136 B2 | 10/2014 | Horvath et al. | |
| 8,852,137 B2 | 10/2014 | Horvath et al. | |
| 8,852,256 B2 | 10/2014 | Horvath et al. | |
| 8,915,877 B2 | 12/2014 | Cunningham et al. | |
| 8,974,511 B2 | 3/2015 | Horvath et al. | |
| 9,017,276 B2 | 4/2015 | Horvath et al. | |
| 9,095,411 B2 | 8/2015 | Horvath et al. | |
| 9,095,413 B2 | 8/2015 | Romoda et al. | |
| 9,113,994 B2 | 8/2015 | Horvath et al. | |
| 9,125,723 B2 | 9/2015 | Horvath et al. | |
| 9,192,516 B2 | 11/2015 | Horvath et al. | |
| 9,271,869 B2 | 3/2016 | Horvath et al. | |
| 9,283,116 B2 | 3/2016 | Romoda et al. | |
| 9,326,891 B2 | 5/2016 | Horvath et al. | |
| 9,375,347 B2 | 6/2016 | Stergiopulos | |
| 9,393,153 B2 | 7/2016 | Horvath et al. | |
| 9,555,410 B2 | 1/2017 | Brammer et al. | |
| 9,585,789 B2 | 3/2017 | Silvestrini et al. | |
| 9,585,790 B2 | 3/2017 | Horvath et al. | |
| 9,592,154 B2 | 3/2017 | Romoda et al. | |
| 9,610,195 B2 | 4/2017 | Horvath | |
| 9,636,254 B2 | 5/2017 | Yu et al. | |
| 9,655,778 B2 | 5/2017 | Tyler | |
| 9,655,779 B2 | 5/2017 | Bigler et al. | |
| 9,693,900 B2 | 7/2017 | Gallardo Inzunza | |
| 9,693,901 B2 | 7/2017 | Horvath et al. | |
| 9,757,276 B2 | 9/2017 | Penhasi | |
| 9,808,373 B2 | 11/2017 | Horvath et al. | |
| 9,877,866 B2 | 1/2018 | Horvath et al. | |
| 9,883,969 B2 | 2/2018 | Horvath et al. | |
| 9,980,854 B2 | 5/2018 | Horvath et al. | |
| 10,004,638 B2 | 6/2018 | Romoda et al. | |
| 10,080,682 B2 | 9/2018 | Horvath et al. | |
| 10,085,884 B2 | 10/2018 | Reitsamer et al. | |
| 10,154,924 B2 | 12/2018 | Clauson et al. | |
| 10,159,600 B2 | 12/2018 | Horvath et al. | |
| 10,195,078 B2 | 2/2019 | Horvath et al. | |
| 10,195,079 B2 | 2/2019 | Horvath et al. | |
| 10,231,871 B2 | 3/2019 | Hill | |
| 10,238,536 B2 | 3/2019 | Olson et al. | |
| 10,285,853 B2 | 5/2019 | Rangel-Friedman et al. | |
| 10,307,293 B2 | 6/2019 | Horvath et al. | |
| 10,314,743 B2 | 6/2019 | Romoda et al. | |
| 10,322,267 B2 | 6/2019 | Hakim | |
| 10,369,048 B2 | 8/2019 | Horvath et al. | |
| 10,405,903 B1 | 9/2019 | Biesinger et al. | |
| 10,463,537 B2 | 11/2019 | Horvath et al. | |
| 10,470,927 B2 | 11/2019 | Horvath et al. | |
| 10,524,959 B2 | 1/2020 | Horvath | |
| 2002/0177891 A1 | 11/2002 | Miles et al. | |
| 2002/0193725 A1 | 12/2002 | Odrich | |
| 2003/0127090 A1 | 7/2003 | Gifford et al. | |
| 2003/0163079 A1 | 8/2003 | Burnett | |
| 2004/0254520 A1 | 12/2004 | Porteous et al. | |
| 2007/0010837 A1 | 1/2007 | Tanaka | |
| 2007/0078371 A1 | 4/2007 | Brown et al. | |
| 2007/0088432 A1 | 4/2007 | Solovay et al. | |
| 2008/0077071 A1 | 3/2008 | Yaron et al. | |
| 2008/0119891 A1 | 5/2008 | Miles et al. | |
| 2008/0125691 A1 * | 5/2008 | Yaron | A61F 9/00781 604/9 |
| 2009/0036818 A1 | 2/2009 | Grahn et al. | |
| 2009/0243956 A1 | 10/2009 | Keilman et al. | |
| 2012/0089073 A1 | 4/2012 | Cunningham, Jr. | |
| 2013/0131577 A1 | 5/2013 | Bronstein et al. | |
| 2013/0150773 A1 | 6/2013 | Nissan et al. | |
| 2013/0150776 A1 | 6/2013 | Bohm et al. | |
| 2013/0158381 A1 | 6/2013 | Rickard | |
| 2013/0199646 A1 | 8/2013 | Brammer et al. | |
| 2013/0205923 A1 | 8/2013 | Brammer et al. | |
| 2013/0267887 A1 | 10/2013 | Kahook et al. | |
| 2013/0317412 A1 | 11/2013 | Dacquay et al. | |
| 2013/0338564 A1 | 12/2013 | Rickard et al. | |
| 2014/0046439 A1 | 2/2014 | Dos Santos et al. | |
| 2014/0081195 A1 * | 3/2014 | Clauson | A61F 9/00781 604/8 |
| 2015/0034217 A1 | 2/2015 | Vad | |
| 2015/0045716 A1 | 2/2015 | Gallardo Inzunza | |
| 2015/0230843 A1 | 8/2015 | Palmer et al. | |
| 2016/0151179 A1 | 6/2016 | Favier et al. | |
| 2016/0256317 A1 | 9/2016 | Horvath et al. | |
| 2016/0256318 A1 | 9/2016 | Horvath et al. | |
| 2016/0256319 A1 | 9/2016 | Horvath et al. | |
| 2016/0256320 A1 | 9/2016 | Horvath et al. | |
| 2016/0354244 A1 | 12/2016 | Horvath et al. | |
| 2016/0354245 A1 | 12/2016 | Horvath et al. | |
| 2017/0027582 A1 | 2/2017 | Khoury et al. | |
| 2017/0071791 A1 | 3/2017 | Piven | |
| 2017/0087016 A1 | 3/2017 | Camras | |
| 2017/0172797 A1 | 6/2017 | Horvath et al. | |
| 2017/0172798 A1 | 6/2017 | Horvath et al. | |
| 2017/0172799 A1 | 6/2017 | Horvath | |
| 2017/0312125 A1 | 11/2017 | Clauson et al. | |
| 2017/0348149 A1 | 12/2017 | Stergiopulos et al. | |

(56) References Cited

U.S. PATENT DOCUMENTS

| | | |
|---|---|---|
| 2017/0348150 A1 | 12/2017 | Horvath et al. |
| 2018/0014828 A1 | 1/2018 | Fonte et al. |
| 2018/0028361 A1 | 2/2018 | Haffner et al. |
| 2018/0092775 A1 | 4/2018 | de Juan, Jr. et al. |
| 2018/0147089 A1 | 5/2018 | Horvath et al. |
| 2018/0206878 A1 | 7/2018 | Uspenski et al. |
| 2018/0250166 A1 | 9/2018 | Lubatschowski |
| 2019/0000673 A1 | 1/2019 | Fjield et al. |
| 2019/0021907 A1 | 1/2019 | Horvath et al. |
| 2019/0038462 A1 | 2/2019 | Vandiest et al. |
| 2019/0046356 A1 | 2/2019 | Laroche |
| 2019/0060118 A1 | 2/2019 | Hill |
| 2019/0133826 A1 | 3/2019 | Horvath et al. |
| 2019/0142632 A1 | 5/2019 | Badawi et al. |
| 2019/0167475 A1 | 6/2019 | Horvath et al. |
| 2019/0240069 A1 | 8/2019 | Horvath et al. |
| 2019/0274881 A1 | 9/2019 | Romoda et al. |
| 2019/0274882 A1 | 9/2019 | Romoda et al. |
| 2019/0344057 A1 | 11/2019 | Cima et al. |
| 2019/0350758 A1 | 11/2019 | Horvath et al. |
| 2019/0353269 A1 | 11/2019 | Ossmer et al. |
| 2020/0069469 A1 | 3/2020 | Horvath et al. |
| 2020/0229980 A1 | 7/2020 | Horvath |
| 2020/0246188 A1 | 8/2020 | Horvath et al. |
| 2020/0261271 A1 | 8/2020 | Horvath et al. |

FOREIGN PATENT DOCUMENTS

| | | |
|---|---|---|
| AU | 2018200325 A1 | 2/2018 |
| AU | 2017274654 | 12/2018 |
| AU | 2020201818 | 4/2020 |
| AU | 2017439185 | 5/2020 |
| AU | 2018412569 | 10/2020 |
| BR | 112017025859 A2 | 8/2018 |
| BR | 112020008969 | 10/2020 |
| CA | 2987953 A1 | 12/2016 |
| CA | 3080713 | 5/2019 |
| CA | 3093160 | 9/2019 |
| CN | 108743016 A | 11/2018 |
| CN | 111405875 | 7/2020 |
| CO | 2020011460 | 11/2020 |
| DE | 10217061 | 3/2003 |
| DE | 102010015447 A1 | 10/2011 |
| DE | 102017124885 A1 | 4/2019 |
| DE | 102018112065 A1 | 11/2019 |
| DE | 102019204846 A1 | 10/2020 |
| EP | 1292256 A1 | 3/2003 |
| EP | 1737531 A2 | 1/2007 |
| EP | 3302381 A1 | 4/2018 |
| EP | 3706653 | 9/2020 |
| ES | 2725550 | 9/2019 |
| HK | 1252748 | 5/2019 |
| HU | E043303 | 8/2019 |
| JP | 5576427 B2 | 8/2014 |
| JP | 2018519892 | 7/2018 |
| JP | 2018130580 | 8/2018 |
| JP | 2019517366 | 6/2019 |
| JP | 2019205934 | 12/2019 |
| JP | 2020049361 | 4/2020 |
| KR | 2018015684 A | 2/2018 |
| KR | 20190019966 | 2/2019 |
| KR | 20200021551 | 2/2020 |
| KR | 20200059305 | 5/2020 |
| PL | 2640455 | 8/2019 |
| PT | 2640455 | 5/2019 |
| RU | 2687764 | 5/2019 |
| RU | 2018142990 | 6/2020 |
| SG | 11202008604 | 10/2020 |
| TR | 201906873 | 6/2019 |
| WO | WO2007011302 A1 | 1/2007 |
| WO | WO2016196841 A1 | 12/2016 |
| WO | WO2018229766 | 12/2018 |
| WO | WO2019018807 | 1/2019 |
| WO | WO2019094004 | 5/2019 |
| WO | WO2019094004 A1 | 5/2019 |
| WO | WO2019172940 | 9/2019 |
| WO | WO2021007294 | 1/2021 |
| WO | WO2021007296 | 1/2021 |
| WO | WO2021028703 | 2/2021 |
| ZA | 201708295 | 5/2020 |

OTHER PUBLICATIONS

International Search Report and Written Opinion received for PCT Application No. PCT/US20/41159, filed Jul. 8, 2020, Applicant: Shifamed Holdings, LLC, dated Oct. 28, 2020, 13 pages.

International Search Report and Written Opinion received for PCT Application No. PCT/US20/41152, filed Jul. 8, 2020, Applicant: Shifamed Holdings, LLC, dated Oct. 28, 2020, 13 pages.

International Search Report and Written Opinion received for PCT Application No. PCT/US20/14186, filed Jan. 17, 2020, Applicant: Shifamed Holdings, LLC, dated Jun. 4, 2020, 13 pages.

International Search Report and Written Opinion received for PCT Application No. PCT/US20/55144, filed Oct. 9, 2020, Applicant: Shifamed Holdings, LLC, dated Feb. 1, 2021, 16 pages.

International Search Report and Written Opinion received for PCT Application No. PCT/US20/55141, filed Oct. 9, 2020, Applicant: Shifamed Holdings, LLC, dated Jan. 29, 2021, 11 pages.

\* cited by examiner

DETAIL B

DETAIL D

DETAIL C

DETAIL D

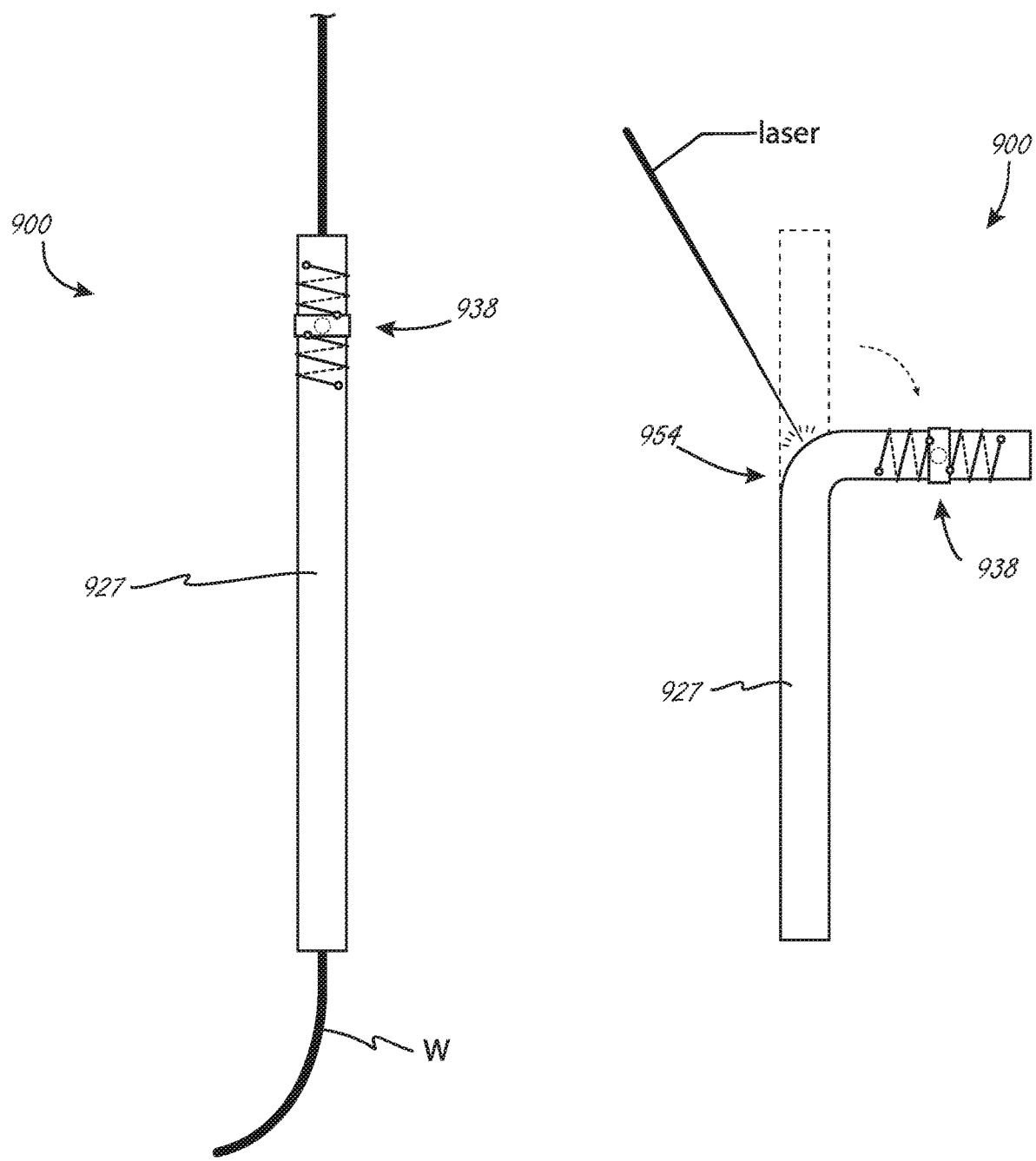

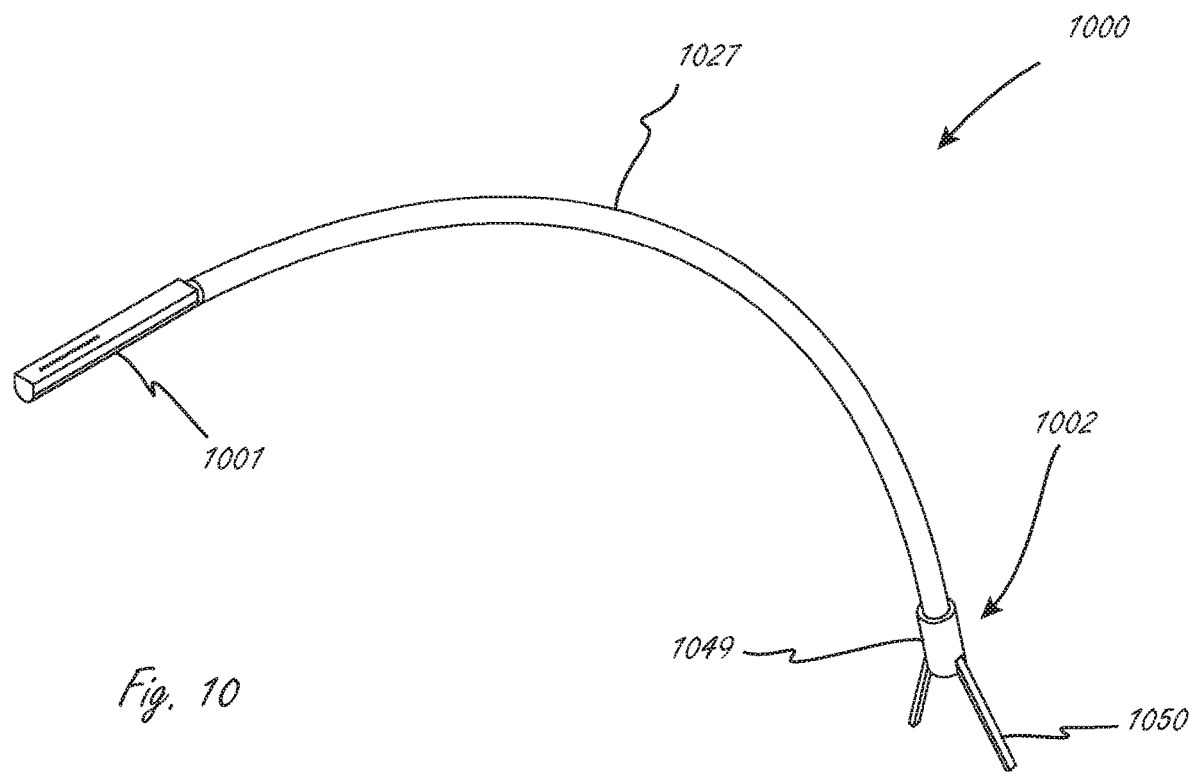
Fig. 10
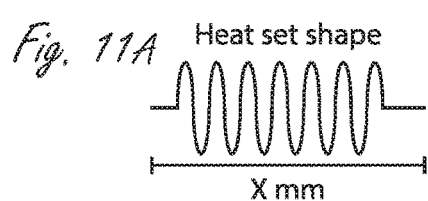
Fig. 11A Heat set shape
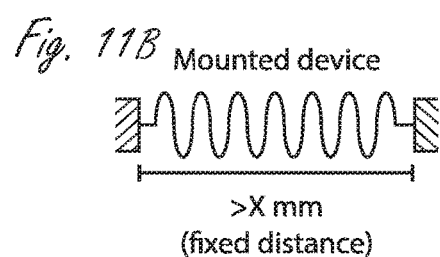
Fig. 11B Mounted device
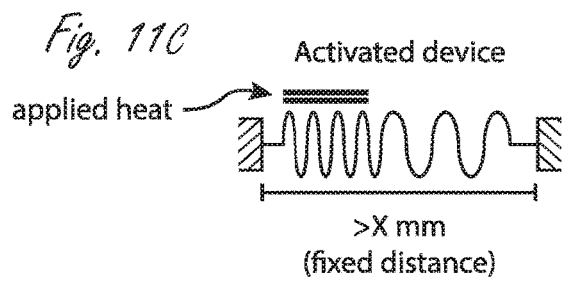
Fig. 11C

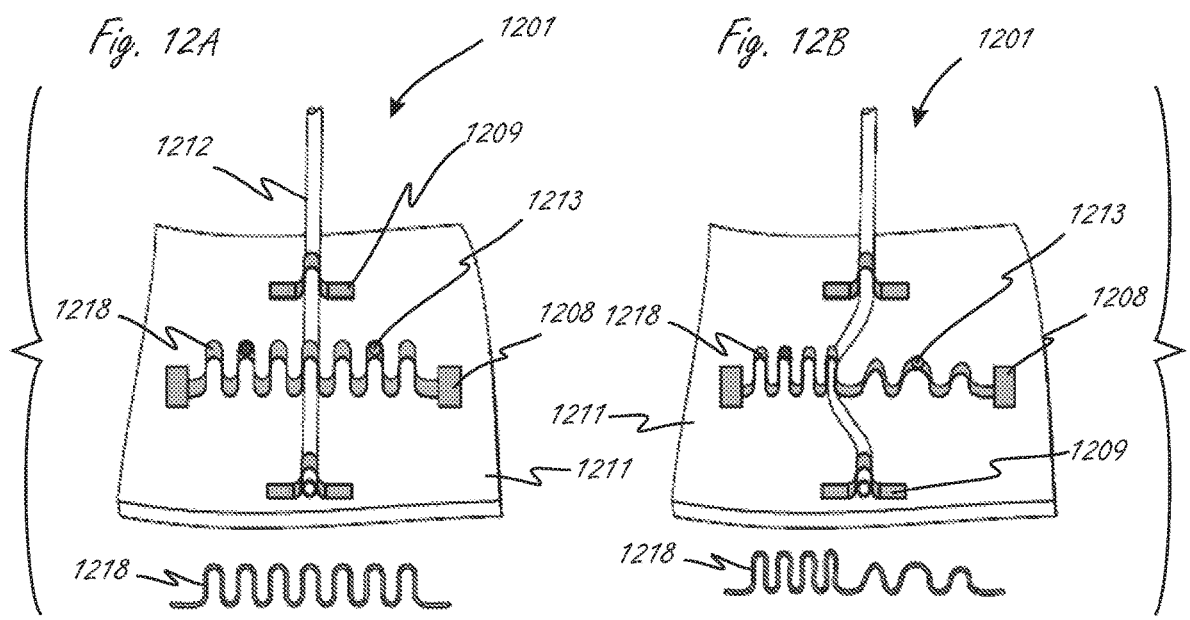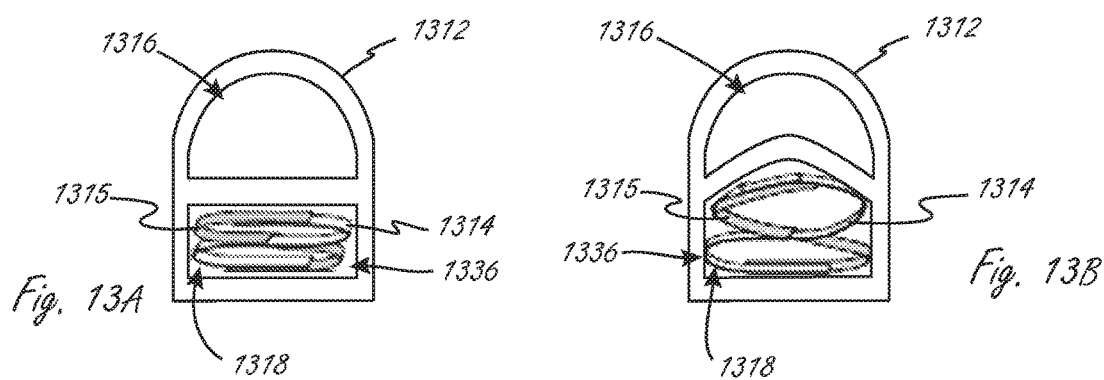

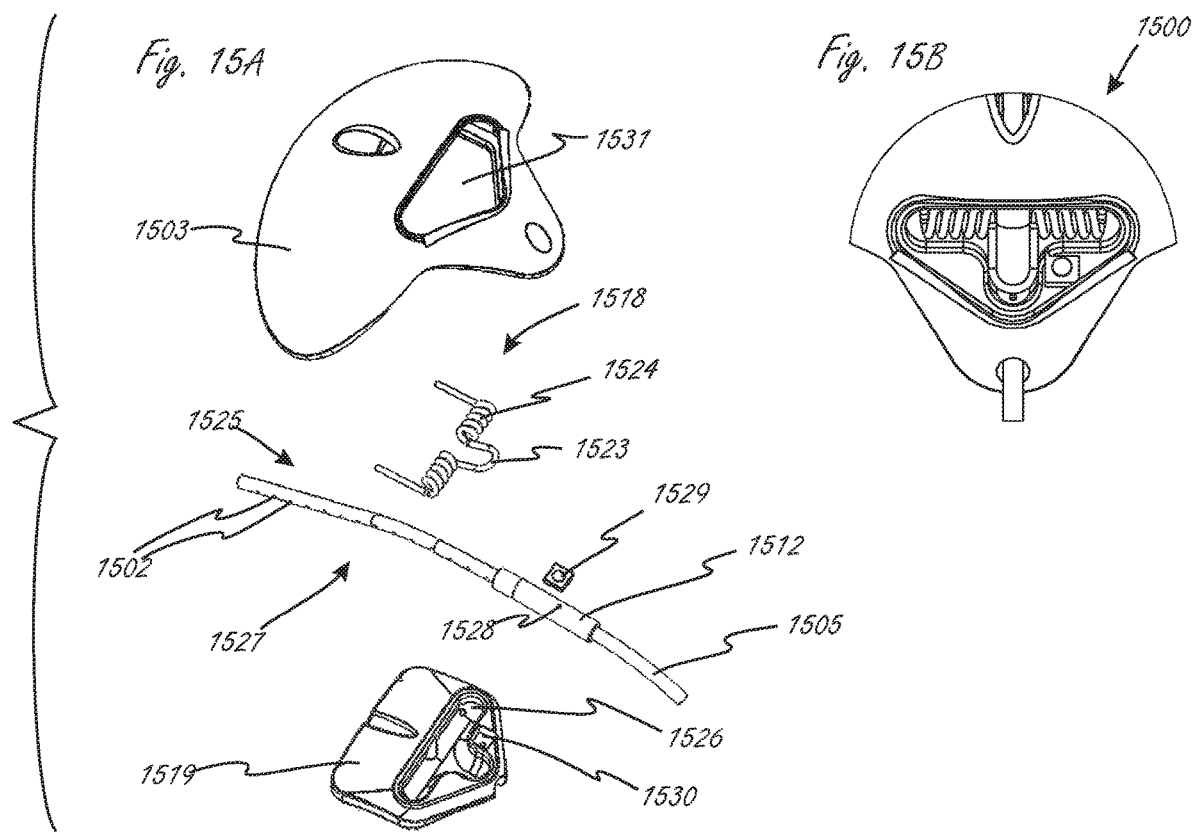
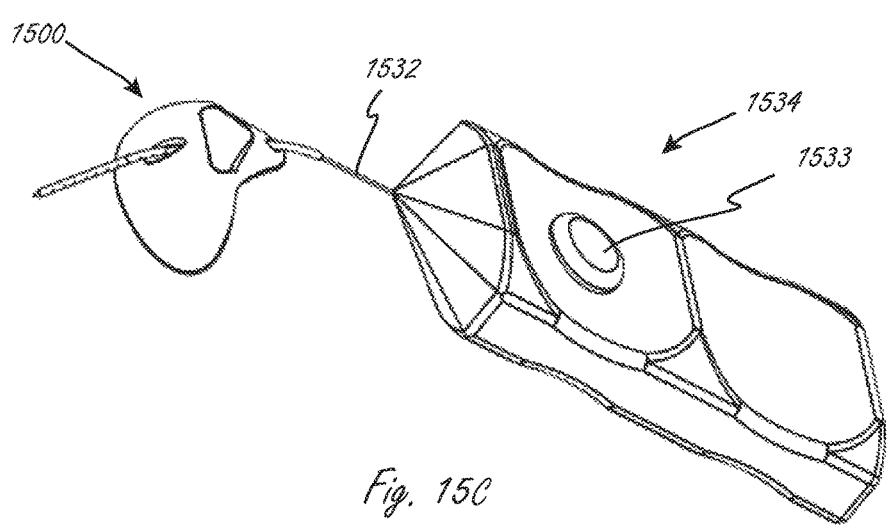

ADJUSTABLE FLOW GLAUCOMA SHUNTS AND METHODS FOR MAKING AND USING SAME

CROSS-REFERENCE TO RELATED APPLICATION(S)

This application is a 35 U.S.C. § 371 U.S. National Phase application of International Patent Application No. PCT/US2018/043158, filed Jul. 20, 2018, and entitled ADJUSTABLE FLOW GLAUCOMA SHUNTS AND METHODS FOR MAKING AND USING SAME, which claims priority to U.S. Provisional Patent Application Nos. 62/643,125, filed Mar. 14, 2018; 62/626,615, filed Feb. 5, 2018, and 62/535,125, filed Jul. 20, 2017, the contents of which are incorporated herein by reference in their entireties.

TECHNICAL FIELD

The present technology relates to adjustable flow glaucoma shunts and methods for making and using such devices.

BACKGROUND

Glaucoma, ocular hypertension, is a disease associated with an increase in pressure within the eye resultant from an increase in production of aqueous humor (aqueous) within the eye and/or a decrease in the rate of outflow of aqueous from within the eye into the blood stream. Aqueous is produced in the ciliary body at the boundary of the posterior and anterior chambers of the eye. It flows into the anterior chamber and eventually into the capillary bed in the sclera of the eye. Glaucoma typically results from a failure in mechanisms that transport aqueous out of the eye and into the blood stream.

Normal aqueous production, for example, is around 2.5 uL/min, and if it is assumed the lowest pressure that can exist in the capillary bed into which the aqueous drains is 0 torr, then maximum outflow resistance in a normal eye at the maximum of normal pressure is expected to be approximately 9 torr/(uL/min). Normal pressure within the eye ranges between 12 torr and 22 torr. As noted above, glaucoma is usually associated with high pressure inside the eye that can damage eye tissues and result in vision loss. The condition where pressures are significantly below this range is called hypotany or ocular hypotension. In some patients, hypotany can be just as damaging (if not more) than glaucoma.

The early stages of glaucoma are typically treated with drugs. When drug treatments no longer suffice, however, surgical approaches are used. Surgical or minimally invasive approaches primarily attempt to lower the outflow resistance of aqueous from the anterior chamber to the blood stream either by the creation of alternative fluid paths or the augmentation of the natural paths for aqueous outflow.

Devices used to lower outflow resistance are generally referred to as "glaucoma shunts" or "shunts." FIGS. 1A-1C, for example, illustrate several different traditional glaucoma plate shunts 100 (identified individually as 100a-c) configured to provide constant resistance to flow. The shunt 100a of FIG. 1A, for example, includes a plate 103a, a plurality of outflow ports 102a, one or more inflow ports 101, and tie-downs or engagement features 104a. The shunts 100b and 100c shown in FIGS. 1B and 1C, respectively, include several features similar to the features of shunt 100a. For example, these shunts 100b-c include plates 103b-c, outflow ports 102b-c, and tie-downs or engagement features 104b-c. The shunts 100b-c, however, include an inflow tube 105 instead of the inflow ports 101 of the shunt 100a.

FIGS. 2A and 2B illustrate a human eye E and suitable location(s) in which shunts 100a-c may be implanted within the eye. More specifically, FIG. 2A is a simplified front view of the eye E, and FIG. 2B is an isometric view of the eye capsule of FIG. 2A. Referring first to FIG. 2A, the eye E includes a number of muscles to control its movement, including a superior rectus SR, inferior rectus IR, lateral rectus LR, medial rectus MR, superior oblique SO, and inferior oblique IO. The eye E also includes an iris, pupil, and limbus.

Referring to FIGS. 2A and 2B together, shunt 100c is positioned such that inflow tube 105 is positioned in an anterior chamber of the eye, and outflow ports 102c are positioned at a different location within the eye. Depending upon the design of the device, the outflow ports 102c may be place in a number of different suitable outflow locations (e.g., between the choroid and the sclera, between the conjunctiva and the sclera). For purposes of illustration, only shunt 100c is shown implanted in the eye E. It will be appreciated, however, that shunts 100a-b may be similarly implanted within the eye E.

Outflow resistance typically depends on the outflow location. Additionally, outflow resistance changes over time as the outflow location goes through its healing process after surgical implantation of the device. Because the outflow resistance changes over time, in many procedures the shunt 100a-c is modified at implantation to temporarily increase its outflow resistance. After a period of time deemed sufficient to allow for healing of the tissues and stabilization of the outflow resistance, the modification to the shunt 100a-c is reversed, thereby decreasing the outflow resistance. Such modifications can be invasive, time-consuming, and expensive for patients. If such a procedure is not followed, however, the likelihood of creating hypotany and its resultant problems is high.

BRIEF DESCRIPTION OF THE DRAWINGS

Many aspects of the present technology can be better understood with reference to the following drawings. The components in the drawings are not necessarily drawn to scale. Instead, emphasis is placed on illustrating clearly the principles of the present technology. Furthermore, components can be shown as transparent in certain views for clarity of illustration only and not to indicate that the component is necessarily transparent. Components may also be shown schematically.

FIGS. 8A-9B illustrate additional embodiments of variable flow glaucoma shunt devices configured in accordance with the present technology.

FIG. 10 illustrates a variable flow shunt device including an actuatable member at an outflow end of the device in accordance with an embodiment of the present technology.

FIGS. 11A-11C illustrate a ribbon or wire composed of shape memory material and configured in accordance with an embodiment of the present technology.

FIGS. 12A and 12B illustrate a fluid control element including variable fluid resistors composed of shape memory materials in accordance with an embodiment of the present technology.

FIGS. 13A and 13B are partially schematic, cross-sectional views of a variable fluid resistor comprising a dual lumen elastomeric tube configured in accordance with an embodiment of the present technology.

FIGS. 15A-15C illustrate an adjustable flow glaucoma shunt configured in accordance with another embodiment of the present technology.

DETAILED DESCRIPTION

Figure 1A:
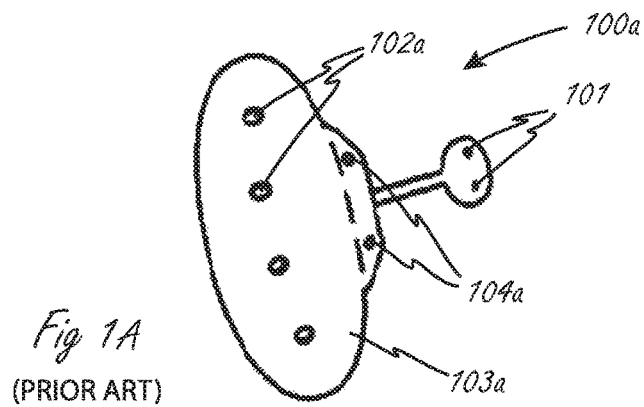
FIGS. 1A-1C illustrate traditional glaucoma plate shunts configured to provide constant resistance to flow.
Figure 1B:
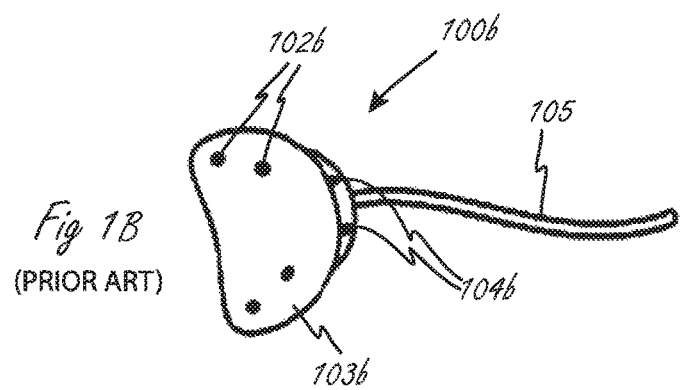
Figure 1C:
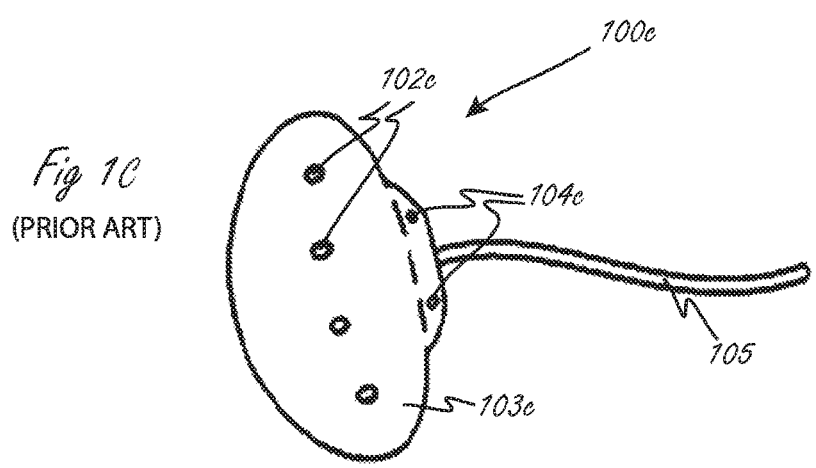
Figure 2A:
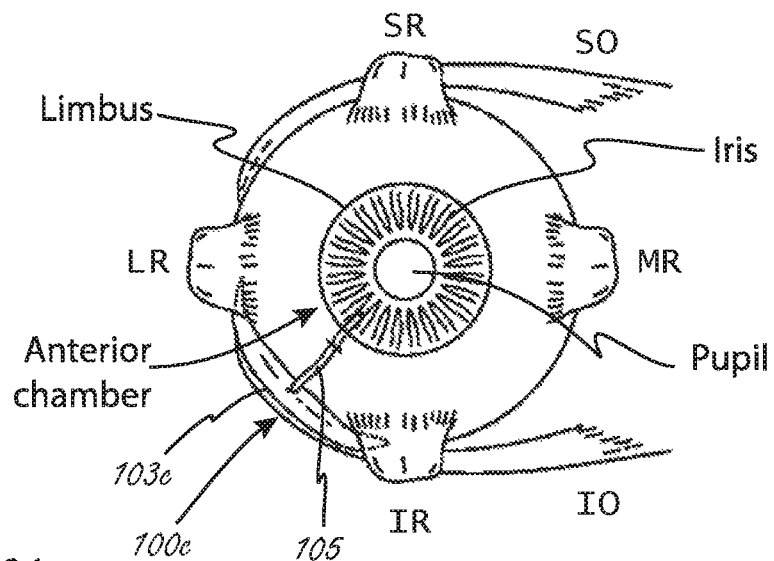
FIG. 2A is simplified front view of an eye E with an implanted shunt.
Figure 2B:
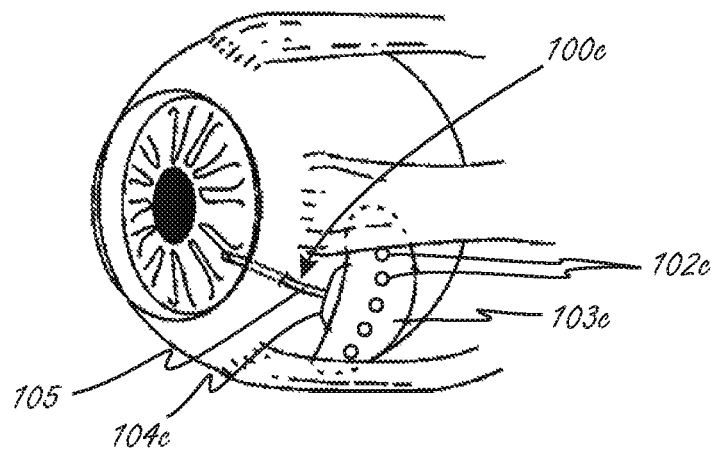
FIG. 2B is an isometric view of the eye capsule of FIG. 2A.

The present technology is directed to adjustable flow glaucoma shunts and methods for making and using such devices. In many of the embodiments disclosed herein, the adjustable flow glaucoma shunts comprise an adjustable fluid resistor ("resistor" within the context of this document refers to a fluid resistor), actuator, and/or actuation mechanism. Additionally, in certain embodiments, the shunts may also include an adjustable opening pressure control mechanism. These mechanisms can be selectively adjusted or modulated to increase or decrease the outflow resistance and/or opening pressure of the shunt in response to changes in any (or any combination of) intraocular pressure (IOP), aqueous production rate, native aqueous outflow resistance, and/or native aqueous outflow rate.

In one embodiment, for example, an adjustable flow shunt for treating glaucoma in a human patient comprises an elongated outflow drainage tube having a proximal inflow region and a distal outflow region. The proximal inflow region can include one or more apertures defining a fluid inlet area positioned to allow fluid to flow therethrough and into the outflow drainage tube. The adjustable flow shunt further comprises an inflow control assembly at the proximal inflow region. The inflow control assembly can include a control element sized and shaped to slidably engage the proximal inflow region and a spring element operably coupled between the control element and an anchor element engaged with the proximal inflow region. The spring element is configured to be activated by a non-invasive energy and, upon activation, slidably move the control element along the proximal inflow region such that (a) the one or more apertures are accessible and have a first fluid flow cross-section or (b) the one or more apertures are at least partially covered by the control element and have a second fluid-flow cross-section less than the first fluid flow cross-section.

In another embodiment of the present technology, an adjustable flow shunt for treatment of glaucoma may comprise an elongated outflow tube having (a) a proximal inflow portion configured for placement within an anterior chamber in a region outside of an optical field of view of an eye of the patient, and (b) a distal outflow portion at a different location of the eye. The adjustable flow shunt also includes an actuator positioned along the outflow tube between the inflow portion and the outflow portion. The actuator is transformable between an open position that allows fluid to flow through the outflow tube and resistance positions that partially obstruct fluid flow through the outflow tube. During operation, the actuator is movable between positions in response to non-invasive energy.

An adjustable flow shunt assembly configured in accordance with still another embodiment of the present technology can include an elongated drainage tube having a proximal portion and a distal portion. The proximal portion includes an inflow port configured to be in fluid communication with a fluid chamber in an eye of the patient. The adjustable flow shunt can also include a variable resistor assembly configured to selectively control flow of fluid into the inflow port. The variable resistor assembly in this embodiment comprises a base portion and an aperture plate carried by the base portion. The aperture plate comprises a plurality of first apertures extending therethrough. The variable resistor assembly also comprises a standoff plate carried by and extending away from the aperture plate. The standoff plate comprises a plurality of second apertures extending therethrough, with the second apertures aligned with corresponding first apertures of the aperture plate. The variable resistor assembly further comprises a membrane disposed on and carried by the standoff plate. The membrane is positioned to sealably cover an open end of each of the second apertures. During operation of the shunt assembly, a portion of the membrane over one or more second apertures of the standoff plate is configured to be selectively targeted and removed via non-invasive energy, thereby creating a fluid path from the site of fluid in the patient through the accessible open ends of the targeted second apertures, the corresponding first apertures, and into the drainage tube.

Specific details of various embodiments of the present technology are described below with reference to FIGS. 3A-16E. Although many of the embodiments are described below with respect to adjustable flow glaucoma shunts and associated methods, other embodiments are within the scope of the present technology. Additionally, other embodiments of the present technology can have different configurations, components, and/or procedures than those described herein. For instance, shunts configured in accordance with the present technology may include additional elements and features beyond those described herein, or other embodiments may not include several of the elements and features shown and described herein.

For ease of reference. throughout this disclosure identical reference numbers are used to identify similar or analogous components or features, but the use of the same reference number does not imply that the parts should be construed to be identical. Indeed, in many examples described herein, the identically numbered parts are distinct in structure and/or function.

Selected Embodiments of Variable Flow Glaucoma Shunts

Figure 3A:
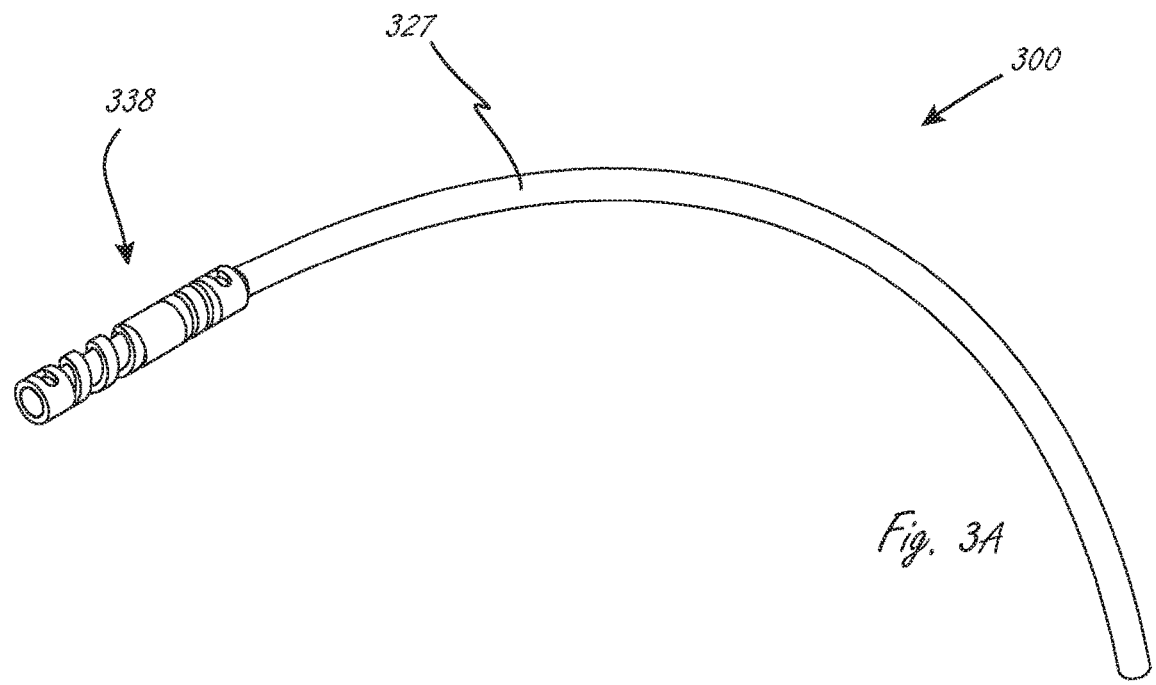
FIGS. 3A and 3B illustrate an adjustable flow glaucoma shunt configured in accordance with an embodiment of the present technology.

FIGS. 3A-16E illustrate a number of different embodiments for variable flow glaucoma shunt devices, along with particular components and features associated with such devices. FIG. 3A, for example, illustrates a variable flow glaucoma shunt 300 ("shunt 300") configured in accordance with an embodiment of the present technology. The shunt 300 includes an inflow control assembly 338 and an outflow drainage tube or outflow assembly 327. The inflow control assembly 338 of the shunt 300 is configured for placement within an anterior chamber in a region outside of the optical field of view of the eye, but within a region visible through the cornea (as described below with reference to FIG. 3C). The outflow drainage tube 327 comprises tubing (e.g., a fine bore length of thin walled tubing) sized and shaped to span the region between the anterior chamber and a desired outflow location. As described in greater detail below, the inflow control assembly 338 comprises a control mechanism configured to act as a variable resistor during operation.

Figure 3B:
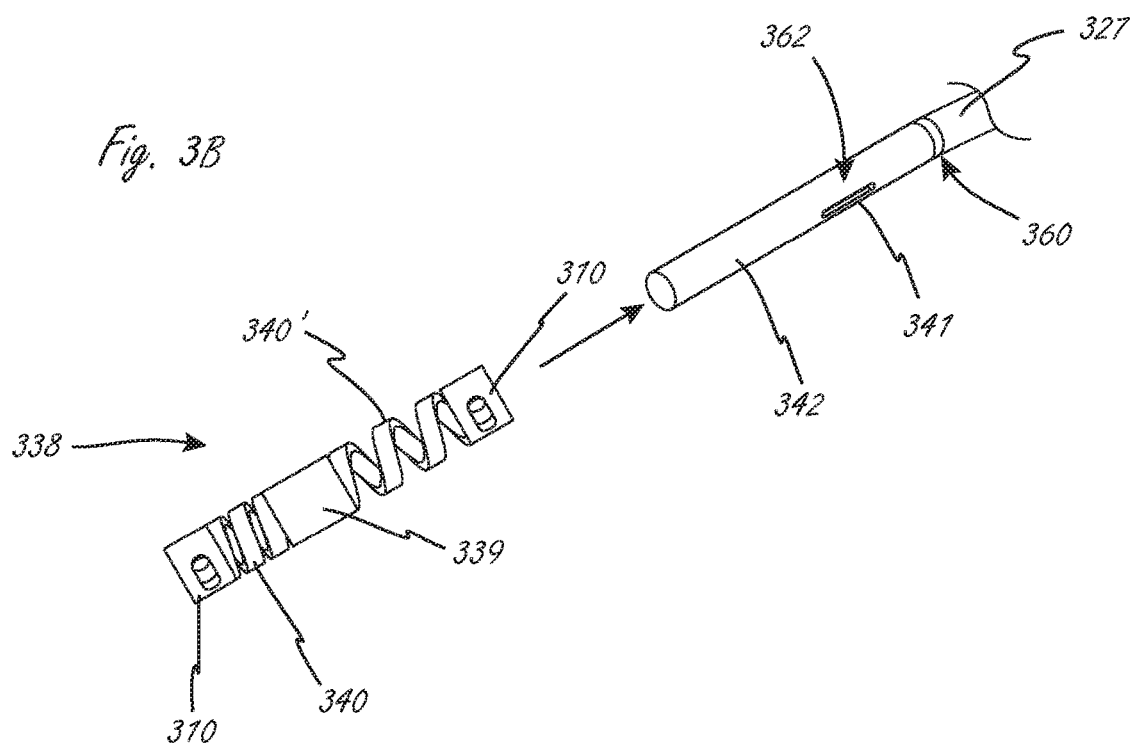

FIG. 3B is a partially exploded view of the shunt 300 with a portion of the inflow control assembly 338 removed from the outflow drainage tube 327 for purposes of illustration. As best seen in FIG. 3B, a proximal end 360 of the outflow drainage tube 327 comprises a proximal inflow region defined by a core element or core feature 342 extending therefrom. The core element 342 may be composed of a relatively stiff material or a combination of stiff materials including, but not limited to, polyether ether ketone (PEEK), acrylic, polycarbonate, metal, ceramic, quartz, and/or sapphire. The portion of the outflow drainage tube 327 not comprised in the core element 342 may be composed of a relatively flexible material (e.g., silicone, urethane, or another suitable material). The core element 342 includes one or more apertures or openings 341 (only one is shown in the illustrated embodiment) that define a fluid inlet area 362. The fluid inlet area 362 is in fluid communication with a lumen of the outflow drainage tube 327. In other embodiments, the aperture(s) 341 may have a different arrangement and/or there may be a different number of apertures 341. For example, in another embodiment the aperture 341 may extend helically about the core element 342. The aperture(s) 341 are positioned to allow fluid to flow therethrough during operation of the shunt 300.

Referring to FIGS. 3A and 3B together, for example, the inflow control assembly 338 in the illustrated embodiment includes a control element 339 configured to be positioned on or around an external surface of the core element 342 (as shown by the arrow in FIG. 3B). During operation, the control element 339 may be adjusted to cover more or less of the fluid inlet area 362. For example, in some embodiments, the control element 339 may be adjusted to increase or decrease the length of a fluid path between an edge of the control section 339 and the aperture(s) 341 (FIG. 3B). In some embodiments, a hydrogel coating may be applied to an inside surface of the control element 339 to further enhance the ability of the control element 339 to slide relative to the core element 342 and enhance sealing of the components during operation. In additional embodiments, the hydrogel coating may also be applied to the core element 342 (in addition to, or in lieu of, application of the coating on the control element 339). Further details regarding adjusting/manipulating the control element 339 are described below.

The inflow control assembly 338 in the illustrated embodiment can also include an adjustable spring element (shown as first and second spring elements 340 and 340') arranged on opposite sides of the control element 339. Each spring element 340 and 340' may further comprise a corresponding anchor element 310.

In the embodiment illustrated in FIGS. 3A and 3B, the control element 339 is composed of a single material. For example, the control element 339 may be fabricated from materials such as (but not limited to) ceramics, alumina oxide, silica oxide, sapphire, and/or quartz. Such materials, for example, may be ground to very high tolerances/precise dimensions. In other embodiments, however, the control element 339 may have different portions/regions composed of different materials. The first and second spring elements 340 and 340' may be composed of a shape memory material (e.g., nitinol or another suitable shape memory material) capable of activation via non-invasive energy, such as light (and or heat). The anchor elements 310 may be fabricated from similar material(s) or other suitable materials.

In operation, first and second spring elements 340 and 340' are configured to be selectivity activated by non-invasive energy and, upon activation, slidably move the control element 339 along the proximal inflow region in a first direction or a second direction, respectively, such that (a) the aperture(s) 341 have a first fluid flow cross-section (e.g., completely open and accessible), or (b) the aperture(s) are at least partially covered by the control element 339 and have a second fluid-flow cross-section less than the first fluid flow cross-section (e.g., partially open/accessible). Further, in some instances the control element 339 may be slidably adjusted such that the aperture(s) 341 are fully covered and inaccessible. One feature of the arrangement shown in FIGS. 3A and 3B is that the inflow control assembly 338 can be selectively adjusted after placement within the eye (e.g., via non-invasive energy) to provide a variety of different outflow resistance levels by incrementally adjusting the control element 339 relative to the aperture(s) 441.

Figure 3C:
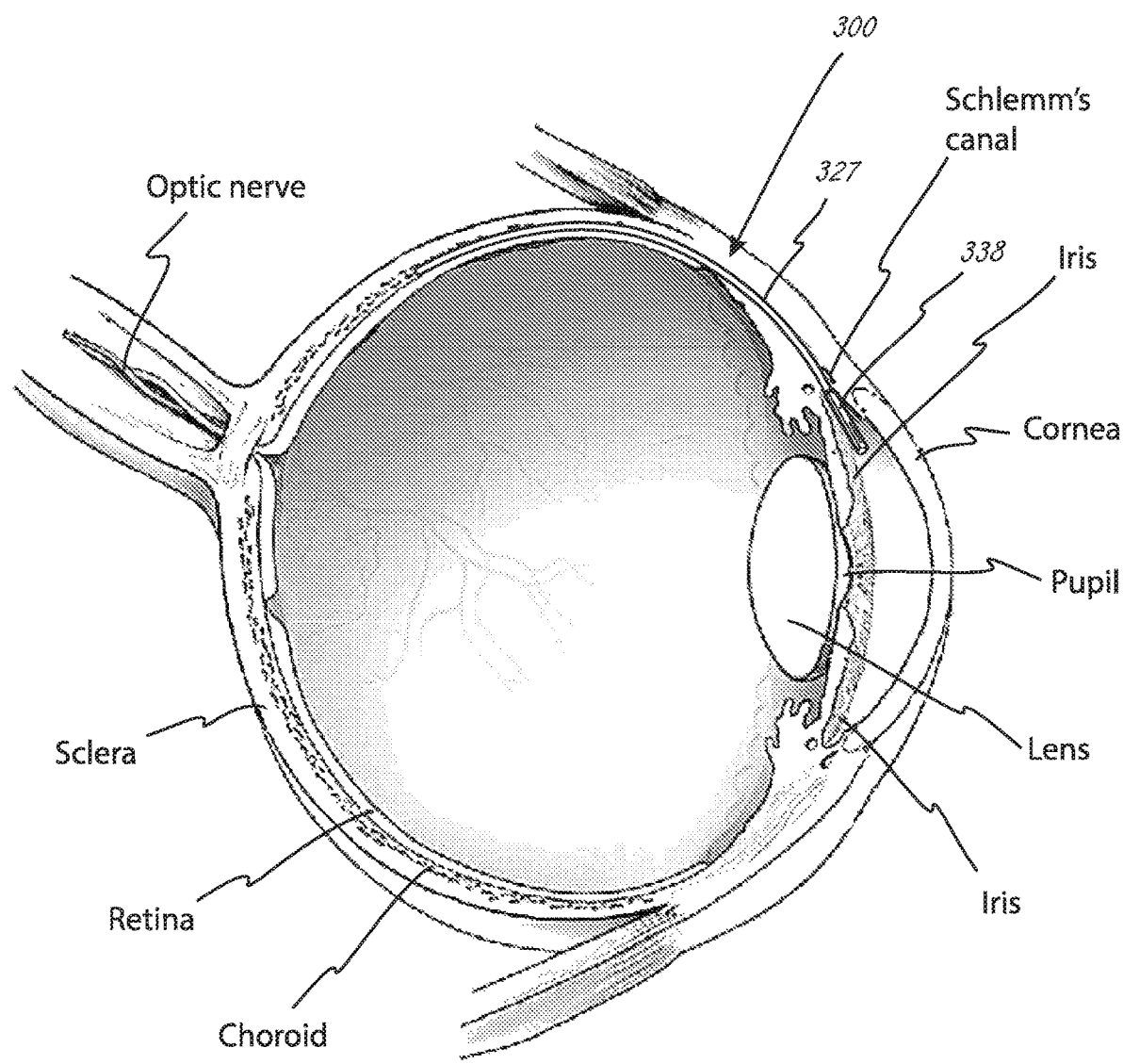
FIG. 3C is a partially schematic illustration of an eye capsule of a human patient showing the adjustable flow glaucoma shunt of FIGS. 3A and 3B implanted within the eye capsule.

FIG. 3C is a partially schematic illustration of an eye capsule of a human patient showing the adjustable flow glaucoma shunt 300 of FIGS. 3A and 3B implanted within the eye capsule. In particular, a typical surgery for implantation of the shunt 100 in the eye capsule comprises the following: (a) a portion of conjunctiva is peeled back; (b) a portion of sclera is removed to create a pocket where the plate is to be placed; (c) the inflow control assembly 338 is routed into the anterior chamber of the eye capsule; (d) the outflow drainage tube 327 is extended through the tissue and into a desired pocket; and (e) the outflow drainage tube 327 and any other portions of the shunt 300 not otherwise buried in the other tissues are covered with conjunctiva. In the embodiment illustrated in FIG. 3C, for example, the shunt 300 is configured for placement traversing a region in the anterior chamber to a region in a suprachoroidal location of the eye. In other embodiments, however, the shunt 300 may be adapted for placement within different portions of the eye. In one embodiment, for example, shunts configured in accordance with the present technology may be positioned at a subconjunctival region within the eye.

Figure 3D:
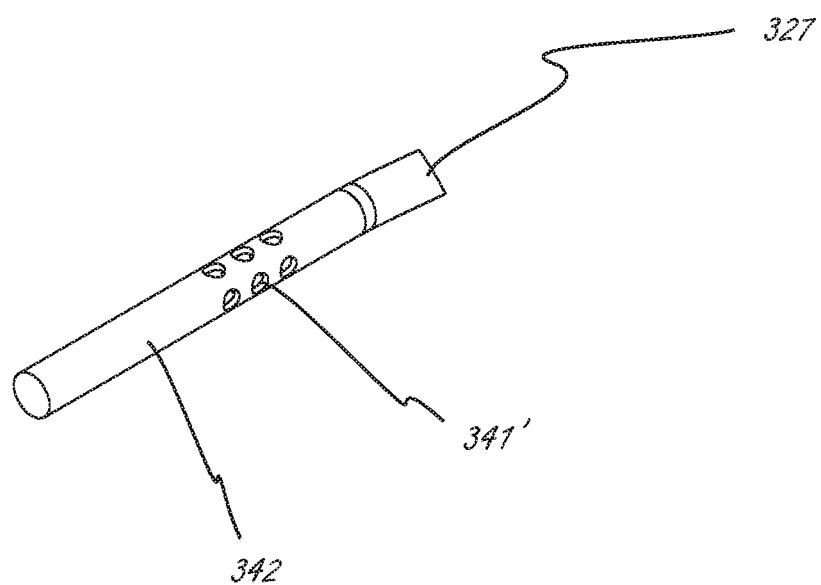
FIGS. 3D and 3E illustrate inflow regions configured in accordance with additional embodiments of the present technology.
Figure 3E:
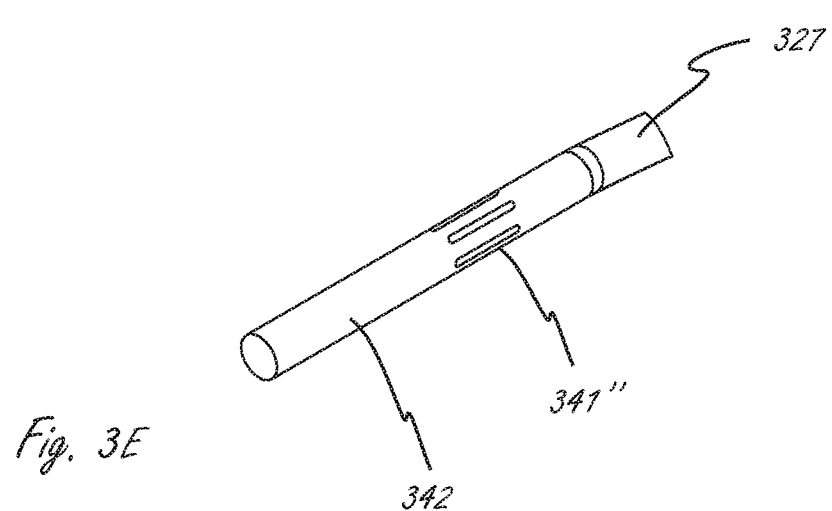

FIGS. 3D and 3E illustrate core elements configured in accordance with different embodiments of the present technology. Referring first to FIG. 3D, for example, core element 342 comprises a plurality of apertures or openings 341' extending therethrough and defining, at least in part, a fluid path in communication with a lumen of the corresponding outflow drainage tube 327. The apertures 341' in the illustrated embodiment have a different arrangement/configuration than the aperture 341 described above with reference to FIGS. 3A and 3B. It will be appreciated that while six apertures 341' are shown in FIG. 3D, the core element 342 may include a different number of apertures 341' in other embodiments. Moreover, the apertures 341' may have a different arrangement relative to each other. FIG. 3E illustrates yet another embodiment of core element 342 having apertures 341" configured in accordance with still yet another arrangement of the present technology. In this embodiment, the apertures 341" comprise a plurality of elongated slots arranged about the core element 342. In other embodiments, the apertures 341'/341" may have a variety of other suitable shapes/sizes.

Figure 4A:
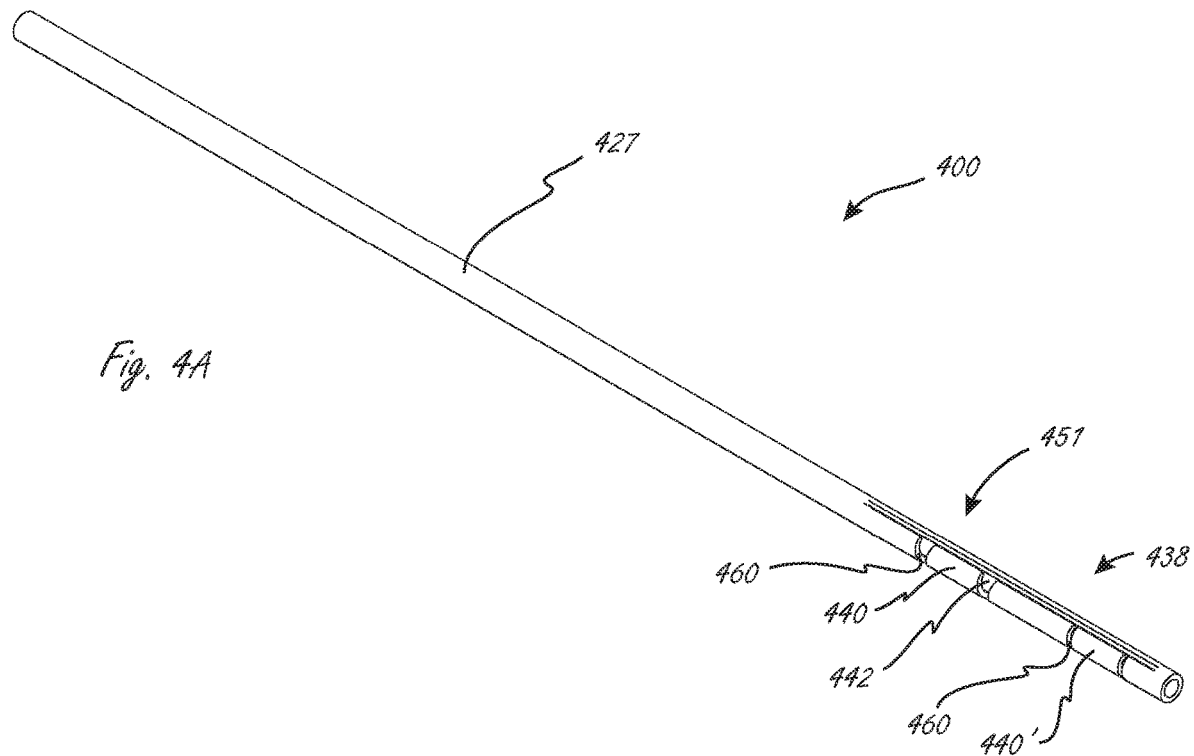
FIGS. 4A-4C illustrate an adjustable flow glaucoma shunt configured in accordance with another embodiment of the present technology.
Figure 4B:
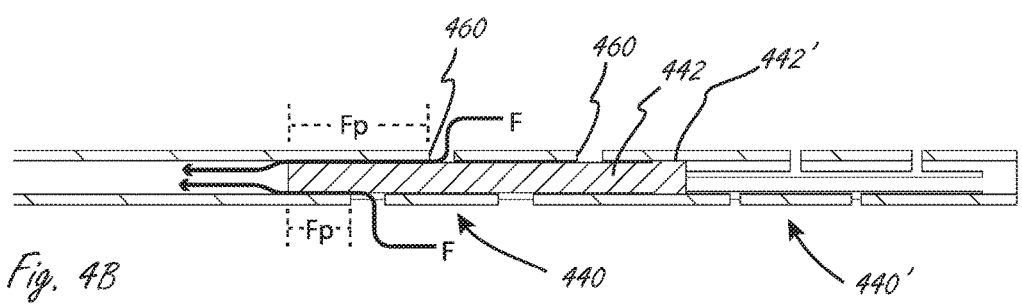
Figure 4C:
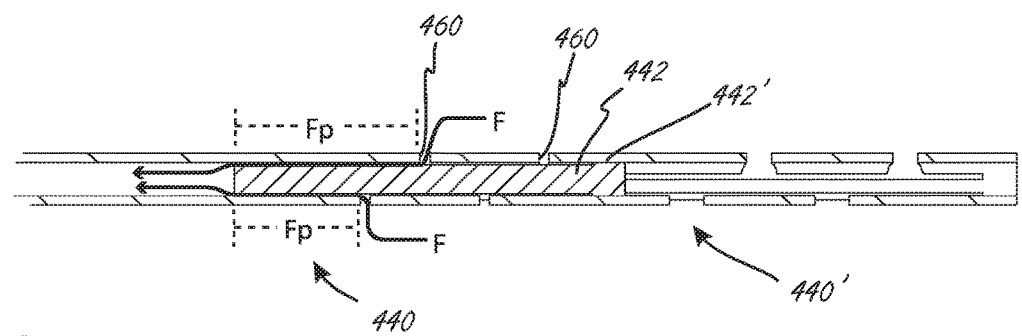

FIGS. 4A-4C illustrate a variable flow glaucoma shunt 400 ("shunt 400") configured in accordance with yet another embodiment of the present technology. The shunt 400 includes an inflow control assembly 438 and an outflow drainage tube or outflow assembly 427. The inflow control assembly 438 includes several features similar to the inflow control assembly 338 of the shunt 300 described above with reference to FIGS. 3A and 3B. For example, inflow control assembly 438 includes a first or proximal spring element 440' and a second or distal spring element 440 arranged adjacent each other. The inflow control assembly 438 further includes a core element or feature 442 coupled to an inner portion of the inflow control assembly 438 at anchor point 442' (as best seen in FIGS. 4B and 4C) between the spring elements 440 and 440'. A fixation spine 451 extends between and is operably coupled to the spring elements 440 and 440'. Although only one fixation spine 451 is shown in the illustrated embodiment, in other embodiments the shunt 400 may include one or more additional fixation spines. In the illustrated embodiment, the fixation spine 451 and first and second spring elements 440 and 440' are all integrally formed from the same tube using a laser cutting process. In other embodiments, however, the spring elements 440 and 440' and/or fixation spine 451 may be separate, discrete components formed from different materials.

In operation, the shunt 400 is configured to operate in an analogous fashion to the shunt 300 described above with respect to FIGS. 3A-3C. In particular, the first and second spring elements 440 and 440' are configured to be selectivity activated by non-invasive energy and, upon activation, slidably move the core element 442 to change the length of a flow path through openings or slits 460 of the inflow control assembly 438. Referring to FIG. 4B, for example, when the distal spring 440 is expanded/actuated, the core element 442 moves proximally and the length of the core portion 442 inside an uncut portion of the shunt 400 (and the corresponding flow F through openings 460 and along flow path FP in the inflow control assembly 438) is at a minimum.

Referring to FIG. 4C, however, when the distal spring 440 is compressed and the proximal spring 440' is expanded/actuated, the length of the core portion 442 inside the uncut portion (and the corresponding flow F along flow path FP) is maximized. The disclosed arrangement is expected to provide an effective and predictable way to incrementally increase/decrease flow resistance in a linear fashion via the shunt 400. In other embodiments, rather than the incremental adjustments in flow rate provided by the shunt 400 shown in FIGS. 4A-4C, the shunt 400 may be configured to provide a binary on/off arrangement via selective actuation of the first and second spring elements 440 and 440'. Further, in some embodiments, the width and/or shape of the openings/slits 460 can be modified to allow for further control of the flow resistance of the shunt 400. In yet another embodiment the core pin may be affixed to the proximal end of spring element 440' and not extend into a flow path. In such an embodiment, the flow path is altered by expanding or compressing the space between the elements of the spring 440 and 440'. In other embodiments, the shape of the pin and or the inner lumen can be modified to change allow for a nonlinear control of flow as a function of core travel.

Figure 5A:
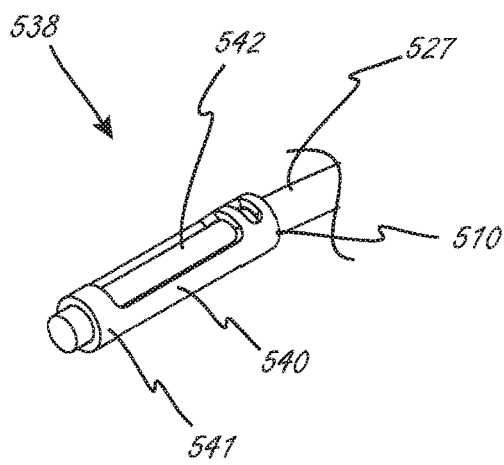
FIGS. 5A-6B illustrate inflow control assemblies configured in accordance with embodiments of the present technology.
Figure 5B:
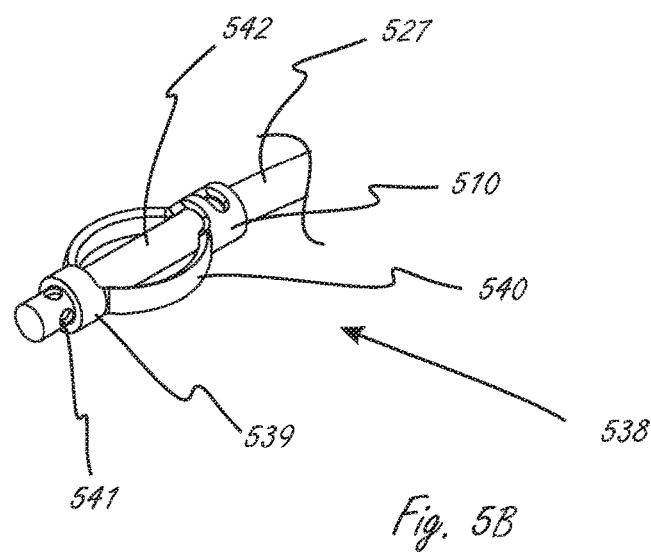

FIGS. 5A-6B illustrate inflow control assemblies configured in accordance with further embodiments of the present technology. Referring first to FIGS. 5A and 5B, for example, inflow control assembly 538 is positioned on or around an external surface of core element 542 at the inflow or inlet region of the drainage tube 527. Inflow control assembly 538 comprises control element 539 and spring elements 540 fixed thereto and extending in a proximal direction toward the drainage tube 527. The inflow control assembly 538 further includes an anchor element 510 operably coupled to the spring elements 540 at a proximal region of the inflow control assembly 538. FIG. 5A illustrates the inflow control assembly 538 in a low or minimum flow configuration in which control element 539 is positioned entirely over or approximately entirely over apertures 541 (FIG. 5B) in the core element 542. FIG. 5B illustrates the inflow control assembly 538 in a maximum flow configuration in which the spring elements 540 have been actuated. In some embodiments, for example, the spring element 540 may be heated via non-invasive energy (e.g., laser energy), thereby causing the spring elements 540 to bow outwardly and slidably move control element 539 in a proximal direction such that apertures 541 are exposed and fluid can flow therethrough into drainage tube 527.

Figure 6A:
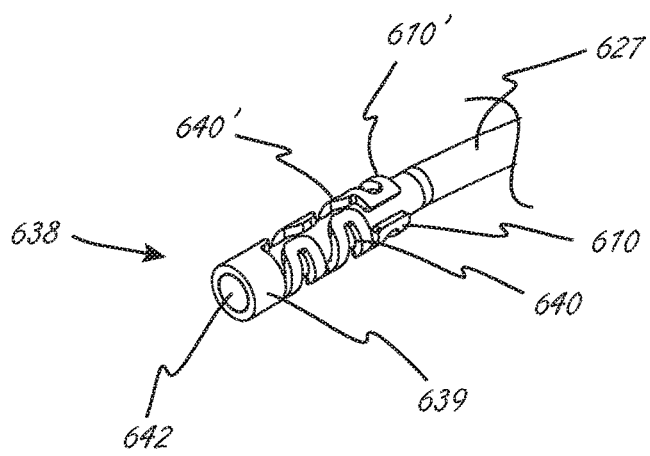
Figure 6B:
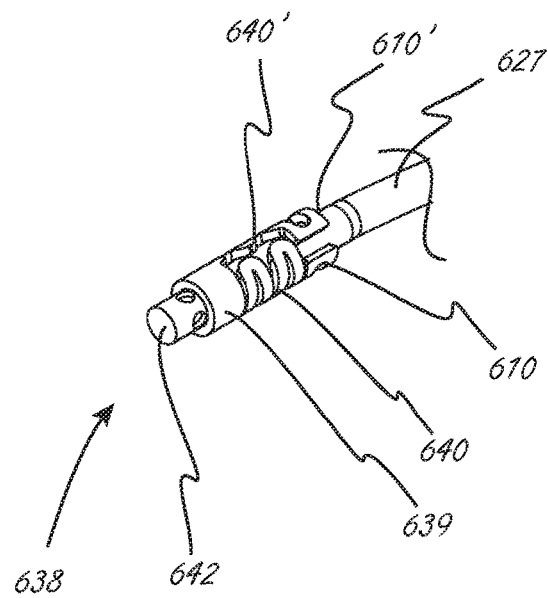

FIGS. 6A and 6B illustrate another embodiment of an inflow control assembly 638 configured in accordance with the present technology. In this embodiment, the inflow control assembly 638 includes a control element 639 and first and second spring elements 640 and 640' fixed thereto and extending in a proximal direction toward the drainage tube 627. The first and second spring elements 640 and 640' have a different configuration than spring elements 540 and 540' described above with reference to FIGS. 5A and 5B. Further, each spring element 640 and 640' is operably coupled to a corresponding anchor element 610 and 610'. Because the individual spring elements 640 and 640' have their own anchor elements 610 and 610', respectively, the spring elements 640 and 640' can be independently set in an initial configuration and independently controlled during operation. As shown in FIG. 6B, for example, the individual spring elements 640 and 640' can be actuated (e.g., via heat), thereby causing the spring elements 640 and 640' to coil more tightly and slidably move control element 639 in a proximal direction along core element 642 and create an open fluid path (to a lumen of drainage tube 627) via exposed apertures 641.

In the embodiments shown in FIGS. 3A-6B, the inflow ends of the various illustrated shunts are sealed. Such shunts may be delivered via a needle (not shown) traversing a desired flow path (as described above with reference to FIG. 3C). In other embodiments, however, the inflow end of a shunt may be initially open (such that the shunt can be delivered over a guide wire) and then sealed after delivery and placement.

Additional Embodiments of Adjustable Flow Glaucoma Shunts

A collection of additional embodiments of adjustable flow and/or adjustable pressure regulated glaucoma shunts comprising plates are described below with reference to FIGS. 7A-16E. Such shunts may be implanted as described above and illustrated in FIG. 3C, or the shunt(s) may be implanted using other suitable techniques and in other suitable locations within the eye. In some of these embodiments, traditional outflow ports are augmented with additional tubes to distribute the aqueous over larger regions of tissue. Outflow tube(s) are covered by at least the conjunctiva. Many of the embodiments of the present technology additionally comprise an adjustable fluid resistor, some of which may additionally comprise an adjustable opening pressure control mechanism. These mechanisms can be adjusted to increase or decrease the outflow resistance and/or opening pressure of the shunt in response to changes in the following: IOP, aqueous production rate, native aqueous outflow resistance, native aqueous outflow rate, and combinations thereof.

Figure 7A:
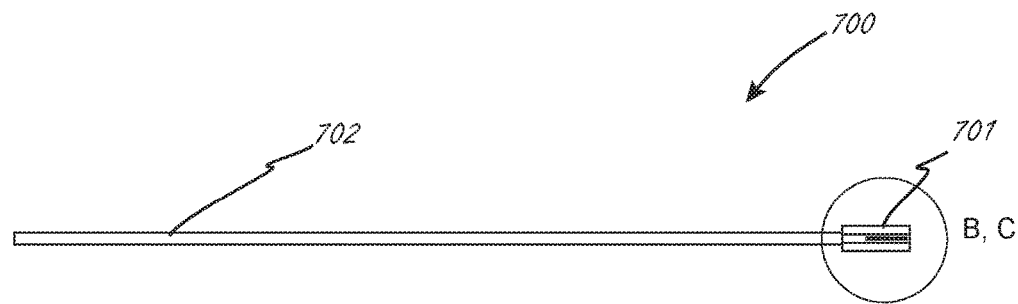
FIGS. 7A-7E illustrate a variable flow shunt configured in accordance with an embodiment of the present technology.

FIGS. 7A-7E illustrate another embodiment of a variable flow shunt 700 configured in accordance with the present technology. FIG. 7A, for example, is a schematic top view of the shunt 700, which is configured for minimally invasive placement (like the shunts described above with reference to FIGS. 3A-6B). The shunt 700 includes an elongated drainage tube 702 having a proximal portion with an inflow port 701 and a distal portion opposite the proximal portion. The shunt 700 differs from the shunts describe above in that fluid resistance of the shunt 700 is selectively controlled by modifying the number of apertures that allow fluid to flow through the inflow port 701. In some embodiments, for example, the shunt 700 can be configured to allow only for sequential decreases in outflow resistance. In other embodiments, however, the shunt 700 may be configured to selectively allow for both finite decreases and increases in outflow resistance. Further details regarding the shunt 700 and its operation are described below.

Figure 7B:
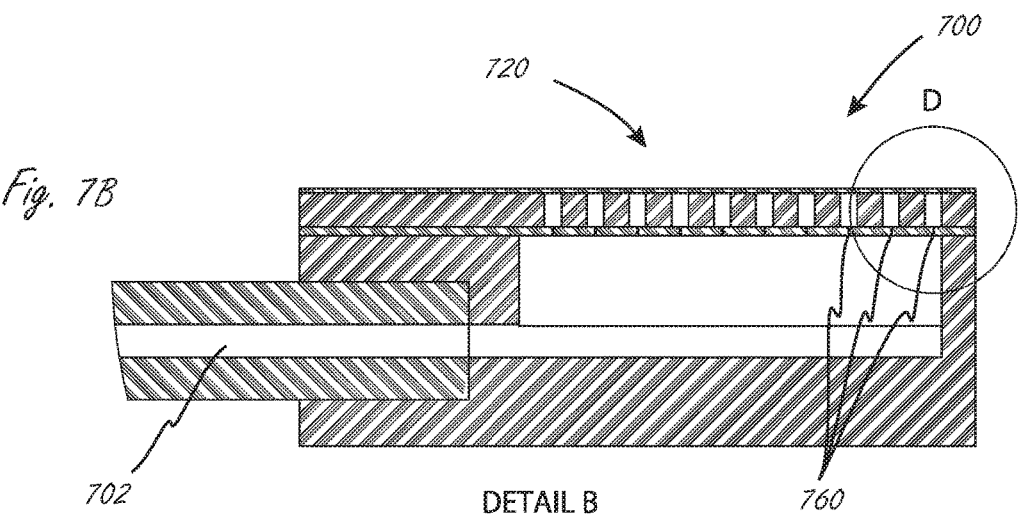
Figure 7C:
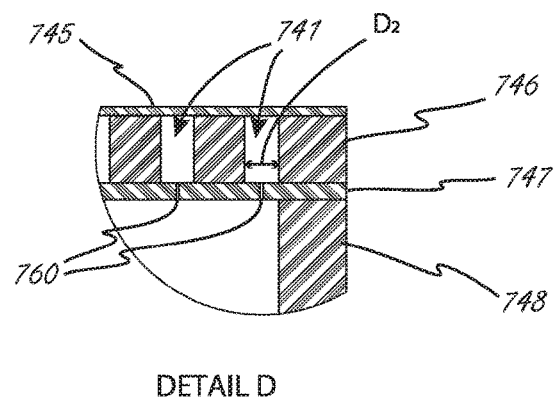

FIG. 7B is an enlarged, partially schematic cross-sectional view of the shunt 700 taken along line B-B of FIG. 7A, and FIG. 7C is an enlarged view of the region C identified in FIG. 7B. Referring to FIGS. 7B and 7C together, the inflow port 701 of the shunt 700 further comprises a variable resistor assembly 720 configured to selectively control flow of fluid into the inflow port (and the outflow port 702). The variable resistor assembly 720 comprises a membrane 745 disposed on and carried by a standoff plate 746. The standoff plate 746 is operably coupled to and extends from aperture plate 747. The aperture plate 747 is carried by a base portion or housing 748 of the shunt 700.

The aperture plate 747 comprises a plurality of first apertures or first openings 760 extending therethrough. The first apertures 760 have a first cross-sectional dimension $D_1$ (not shown). The first apertures 760 can be precisely formed so that each opening is identical or nearly identical and all of the first apertures 760 are a predetermined size. The standoff plate 746 comprises a plurality of second apertures or second openings 741 extending therethrough. The second apertures 741 have a second cross-sectional dimension $D_2$ larger than the first cross-sectional dimension $D_1$. As will be described in greater detail below, the second apertures 741 do not need to be as precisely formed as the first apertures 760. As shown in FIG. 7C, the membrane 745 completely covers one end (an upper or first end) of each of the second apertures 741. The opposite end of each second aperture 741 (a second or lower end) is aligned with a corresponding first aperture or first opening 760 extending through the aperture plate 747.

Figure 7D:
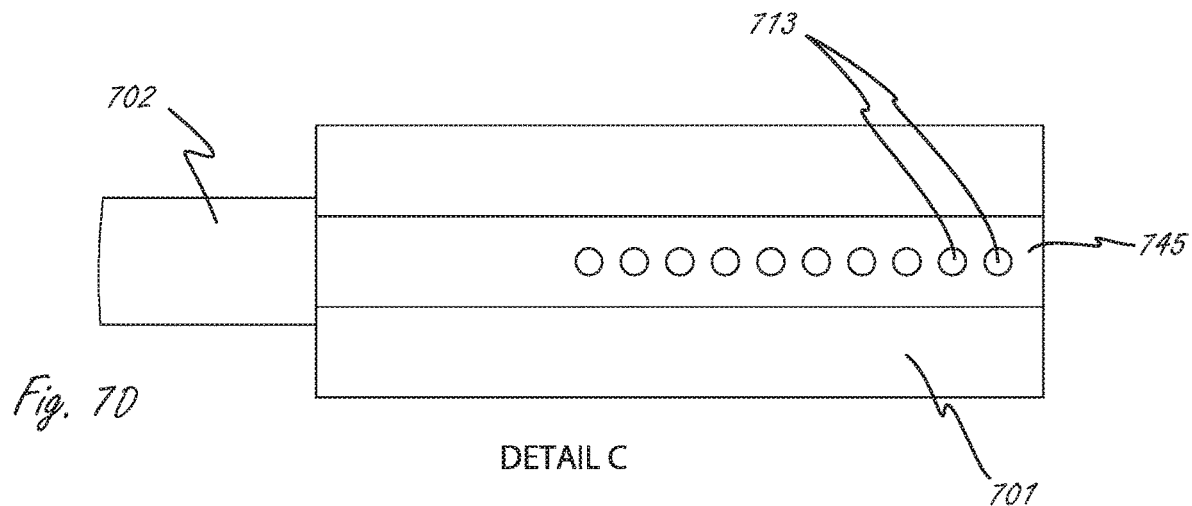
Figure 7E:
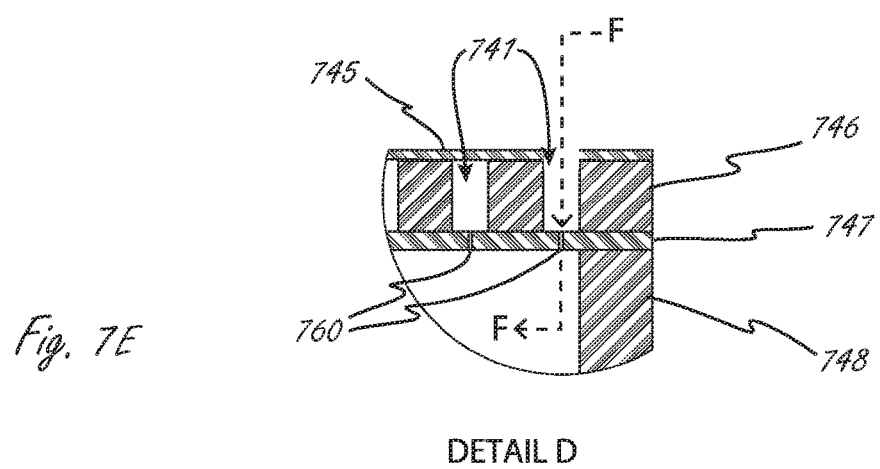

FIG. 7D is a top view of the variable resistor assembly 720. As best seen in FIG. 7D, the variable resistor assembly 720 further comprises a plurality of target indicia or markers 713 ("targets 713"). The individual targets 713 correspond to and are aligned with each first aperture 741 (FIG. 7B). Referring next to FIG. 7E, after the shunt 700 is implanted within a patient and it is desired to reduce the fluid resistance of the shunt 700, non-invasive energy (e.g., a surgical laser) can directed at a selected target 713 on membrane 745. In embodiments using laser energy, for example, the laser can be activated or fired to selectively ablate the targeted material of the membrane 745, thereby removing such membrane material and exposing the open end of the corresponding second aperture 741. Without the membrane blocking the targeted second aperture 741, fluid can flow therethrough (as shown by the arrow F), and subsequently through the corresponding first aperture 760 and into the outflow drainage tube 702. If a further reduction in fluid resistance is desired, one or more additional targets 713 on membrane 745 may be ablated to expose additional second apertures 741 and allow additional fluid to flow therethrough to outflow drainage tube 702.

In the illustrated embodiment, outflow resistance can only be lowered as there is no means of sealing the second apertures 741 of the implanted shunt 700 once the corresponding targeted portions of the membrane 745 are removed to open the second aperture(s) 741 to aqueous flow. In other embodiments, however, there may be techniques to later impede or stop fluid flow by blocking one or more open second apertures 741. For example, referring to FIGS. 7B and 7C, in some embodiments the membrane 745 and standoff plate 746 may be composed, at least in part, from a hydrophobic material (e.g., a low melting point wax) adapted to be melted by the surgical laser (not shown) at temperatures that will not cause particular harm to the aqueous. In such embodiments, a relatively small, fine beam from the laser source can be used to melt the wax material of the target membrane 754 and open the corresponding second aperture 741. At a later point in time, if it is desired to slow or limit flow of aqueous, a larger beam from the laser source can be used to melt the wax material of the standoff plate 746, thereby causing the material to "puddle" or accumulate over the corresponding second aperture 760 within the previously opened second aperture 741 and close or block fluid flow through the first aperture 760.

In the embodiment illustrated in FIGS. 7A-7E, the components of the variable resistor assembly 720 are separate, discrete components that are operably coupled together before implantation of the shunt 700. The components may be composed of similar materials, or one or more different materials. In other embodiments, however, the membrane 745 and standoff plate 746 may be fabricated as a single unitary component composed of the same material, such as the example described above in which the membrane 745 and standoff plate 746 comprise a unitary component composed of a hydrophobic material. In other embodiments, however, the integral membrane 745/standoff plate 746 may be composed of other suitable materials. In still other embodiments, the standoff plate 746 and aperture plate 747 may be fabricated of a single unitary component composed of the same material with the first and second apertures 741 and 760 formed therein. In yet additional embodiments, the aperture plate 747 may be integrally formed with the base portion 748 of the shunt 700.

Figures 8A, 8B:
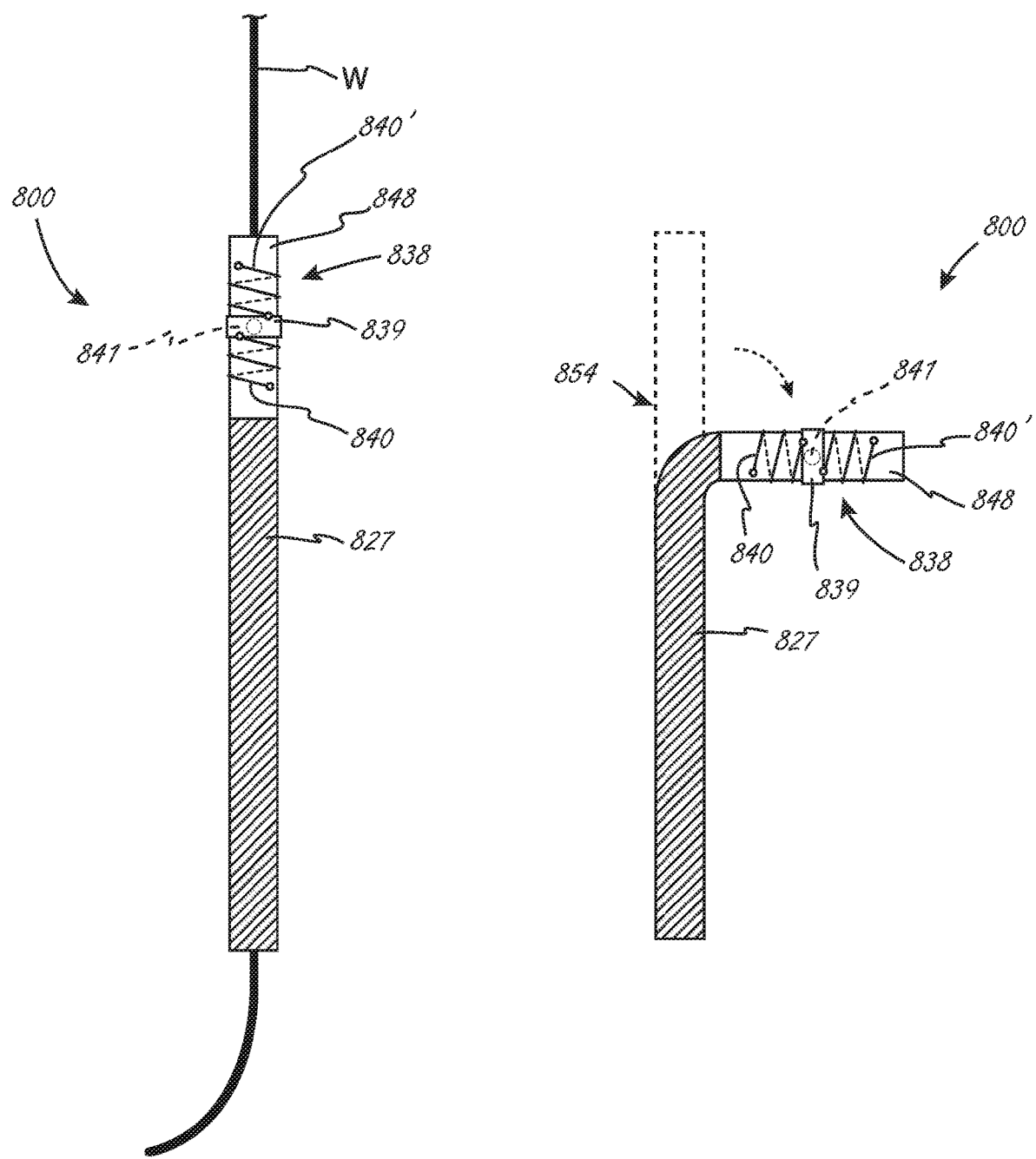

FIGS. 8A-9B illustrate additional embodiments of variable flow glaucoma shunt devices configured in accordance with the present technology. In these embodiments, the shunts are configured to be delivered to a target location within an eye capsule of the patient via a guidewire, and then transformed between a delivery configuration and a deployed configuration upon removal of the guidewire. FIG. 8A, for example, illustrates shunt 800 in a delivery configuration on guidewire W. The shunt 800 includes an inflow control assembly 838 and an outflow tube or outflow assembly 827. The inflow control assembly 838 can include several features generally similar to the shunts described above with reference to FIGS. 3A-6B. For example, the shunt 800 includes a control element 839 positioned over one or more apertures or openings 841 (shown in broken lines) extending through a body portion 848 of the inflow control assembly 838. The aperture(s) 841, when at least partially exposed, are configured to allow aqueous to flow therethrough and into the outflow tube 827. The shunt 800 also comprises a pair of adjustable spring elements 840 and 840' arranged on opposite sides of the control element 839. The spring elements 840 and 840' are coupled between the body portion 848 and the control element 839. In some embodiments, the spring elements 840 and 840' are composed of a shape memory material (e.g., nitinol) and adapted to expand/contract when heat is applied. For example, applying heat to the first spring element 840 can induce this spring element to coil more tightly, thereby moving the control element 839 toward the first spring element 840 and stretching or expanding the second spring element 840'. Moving the control element 839 also at least partially exposes the aperture(s) 841 to allow aqueous to flow therethrough similar to the techniques described above with reference to FIGS. 3A-6B.

In the illustrated embodiment, the inflow control assembly 838 is composed of a first material having a first rigidity and the outflow tube 827 is composed of a second material having a second rigidity less than the first rigidity. Referring to FIGS. 8A and 8B together, the shunt 800 may be preshaped prior to implantation such that the shunt 800 includes one or more bends along its length. In the illustrated embodiment, for example, the shunt 800 comprises a generally "L" shaped arrangement and includes a bend or elbow 854 at or near a distal region of the outflow tube 827.

When the shunt 800 is positioned on guidewire W for delivery, the shunt 800 assumes a generally linear, straight delivery configuration. As shown in FIG. 8B, however, when the guidewire W is removed, the shunt 800 transforms between its delivery configuration and an expanded/deployed configuration in which the shunt 800 assumes its predetermined "L" shaped arrangement including elbow 865. This configuration is expected to allow for rapid and reliable delivery of the shunt 800 via guidewire W, and enable precise placement of the inflow control assembly 838 within the eye capsule of the patient once the guidewire is removed and the shunt 800 assumes is predetermined shape.

FIGS. 9A and 9B illustrate a shunt 900 configured in accordance with still another embodiment of the present technology. The shunt 900 includes a number of features generally similar to the features of shunt 800. The shunt 900 differs from shunt 800 in that the shunt 900 is not composed of different materials having different rigidities. Rather, the shunt 900 comprises an inflow portion or region 938 and an outflow portion or outflow tube 927 composed of a single material (e.g., a shape memory material such as nitinol). The shunt 900, like shunt 800 described above, also includes a preset, generally "L" shaped arrangement and includes a bend or elbow 954. In this embodiment, however, removing the guidewire W does not transform the shunt 900 between its delivery configuration (FIG. 9A) and its deployed/expanded configuration (FIG. 9B). Instead, as best seen in FIG. 9B, once guidewire W is removed and the shunt 900 is at a desired location within the patient, a laser source (e.g., an ophthalmic laser—not shown) can be used to direct a laser beam to selectively heat a portion of the shunt 900 and induce the shunt 900 to bend about elbow 954 and return to its preset shape (the generally "L" shaped arrangement).

FIG. 10 illustrates a variable flow shunt device 1000 configured in accordance with yet another embodiment of the present technology. The shunt 1000 comprises an inflow assembly 1001 and an outflow drainage tube 1027 with an outflow port 1002. The shunt 1000 further comprises an actuatable member 1049 at the outflow end of the outflow port 1002 (opposite the inflow assembly 1001). The actuatable member 1049 comprises one or more tissue disruption members 1050 (e.g., barbs or other suitable types of devices) to disrupt/disturb tissue at or proximate the outflow end of the outflow port 1001 after the shunt 1000 is implanted within the patient. In one embodiment, the barbs 1050 of the actuatable member 1049 can be moved and actuated by an operator via an externally applied magnetic field to disrupt target tissue adjacent the outflow end of the shunt 1000. In other embodiments, however, the barbs 1050 may be moved/actuated using other suitable techniques, such as thermally induced shape changes. Further, it will be appreciated that a different number of barbs 1050 may be used and/or the barbs 1050 may have a different arrangement relative to each other and the actuatable member 1049.

Many of the embodiments disclosed herein make use of a shape memory material (SMM), such as nitinol, shape memory polymers, and the like, as a control in an adjustable fluid resistor. As noted previously, such fluid resistors allow controlled flow of aqueous from within the anterior chamber of the eye to a location into which the aqueous can defuse. One such location is within or on top of the sclera posterior to the cornea. In general, SMM elements utilized in the various devices disclosed herein can be repeatedly activated in one direction to increase fluid resistance and in another direction to decrease fluid resistance. In some embodiments, for example, each of multiple activations on targets in one section of the actuation element will incrementally increase the resistance, while multiple activations on targets in another section of the actuation element will incrementally decrease the resistance. When a target is heated above its transition temperature, such as by heating via non-invasive laser energy, the SMM shifts from its larger volume, lower stiffness, low temperature martensite (Mar) form to its high temperature, smaller volume, stiffer austenite form (Aus).

Aus (austenite) 75-83 GPa, smaller volume, high temperature

Mar (martensite) 28-40 GPa, larger volume, low temperature

One such configuration is illustrated in FIGS. 11A-11C, which represents a side view of a ribbon or wire configured in accordance with embodiments of the present technology. Referring first to FIG. 11A, the ribbon has been shape-set in a form comprising multiple uniform folds. As illustrated, there are six folds, but it will be appreciated that in other embodiments ribbons with more or less folds can be used depending on the desired amount of resolution and displacement. Referring next to FIG. 11B, the ribbon can then be mounted between two anchors such that the constrained length is larger than the heat set length. Referring now to FIG. 11C, applying heat to the fold(s) in the portion of SMM heated above its Aus, shifts it from its less stiff, higher volume Mar form to its stiffer and lower volume Aus form. In the illustrated embodiment, the entire SMM component is not allowed to return to its heat set shape even if the entire portion of SMM is heated above the transformation temperature. The unheated portion can expand further to compensate. In addition, heating previously unheated sections is expected to stretch previously unheated and heated sections reversing the mechanism.

FIGS. 12A and 12B illustrate a fluid control element 1201 configured in accordance with another embodiment of the present disclosure. The fluid control element 1201 may be used with any of the variable flow shunts described herein or other suitable shunts. In this embodiment, the fluid control element 1201 comprises variable fluid resistors actuated by SMM elements (like those described above with reference to FIGS. 11A-11C). Referring first to FIG. 12A, fluid control element 1201 comprises a base 1211 and a flow-through drainage tube 1212 carried by and operably coupled to the base 121. For example, the flow-through tube 1212 can be fixed to the base 1211 via flow-through anchors 1209. In other embodiments, however, other suitable techniques may be used to secure the flow-through tube 1212 to the base 1211. The flow-through tube 1212 is also operably engaged with an actuator 1218. In the illustrated embodiment, the actuator 1218 comprises a ribbon or wire composed of SMM and including a plurality of folds. The actuator 1218 has a fixed length and each end of the actuator 1218 is anchored to the base 1211.

The actuator 1218 may be actuated using techniques similar to those described above with reference to FIGS. 11A-11C. During operation, for example, the tops of the folds along the actuator 518 may be used as target regions to be selectively heated via non-invasive energy (e.g., laser energy) to locally heat such regions along the actuator 518. As discussed previously with respect to FIGS. 11A-11C, heating folds on one side relative to the other side will allow incremental shifting of resistance (up or down) to modify the state of the actuator 1218, and thereby change fluid resistance through the flow-through tube 1212. FIG. 12A, for example, illustrates a low-resistance state of the fluid control element 1201 in which the actuator 1218 is fairly uniform along its length and provides minimal resistance or interference with fluid flow through the flow-through tube 1212. FIG. 12B illustrates a high resistance state of the of the fluid control element 1201. The high resistance state or high resistance position is a result, for example, of multiple actuations via the actuation element 1218 to the flow-through tube 1212. In particular, heating each of the folds of the actuation element 1218 on the left side of the flow-through tube 1212 above the actuation temperature causes the actuation element 1218 in this region to shrink, thereby "pinching" and compressing the flow-through tube 1212 in this direction and increasing fluid resistance therethrough. When desired, fluid control element 1201 can be transformed again to additional resistance positions or orientations than that shown in FIG. 12B (e.g., back to the state shown in FIG. 12A or a different state) via further manipulation/modulation (e.g., heating selected regions) of actuation element 1218.

FIGS. 13A and 13B are partially schematic, cross-sectional views of a variable fluid resistor comprising a dual lumen elastomeric tube 1312 configured in accordance with still another embodiment of the present technology. More specifically, FIG. 13A illustrates the elastomeric tube 1312 in an initial or low-resistance state before modulation. The elastomeric tube 1312 comprises a first lumen or a fluid flow-through lumen 1316 having an initial cross-sectional shape (e.g., a "D" shaped lumen). The elastomeric tube 1312 further comprises a second lumen or a control lumen 1336 adjacent the first lumen 1316 and a diaphragm therebetween. The control lumen 1336 contains one or more actuation elements 1318. In the illustrated embodiment, for example, the actuation element 1318 is composed of SMM and includes a first or expansion portion 1314 and a second or shrinkage portion 1315. Although only a single actuation element 1318 is shown in the cross-sectional views of FIGS. 13A and 13B, it will be appreciated that in further embodiments multiple actuation elements 618 can be arrayed serially along a length of the elastomeric tube 1312.

FIG. 13B illustrates the elastomeric tube 1312 in an increased or higher resistance state after activation of the actuation element 1318. More specifically, non-invasive energy (e.g., heating via laser energy) has been used on expansion portion 1314 of the actuation element 1318, thereby causing the actuation element 1318 to expand. Such expansion pushes the diaphragm toward the flow-through lumen 1316 and decreases the cross-sectional dimension of the flow-through lumen 1316. This decrease in size of the flow-through lumen 1316 accordingly increases the fluid resistance through the lumen 1316. The cross-sectional dimension of the flow-through lumen 1316 can be further modified via additional modulation of the actuation element 1318. For example, fluid resistance through the flow-through lumen 1316 can be further decreased by additional heating of the expansion portion 1314 or returned to a lower resistance state via heating of the shrinkage portion 1315.

Figure 13C:
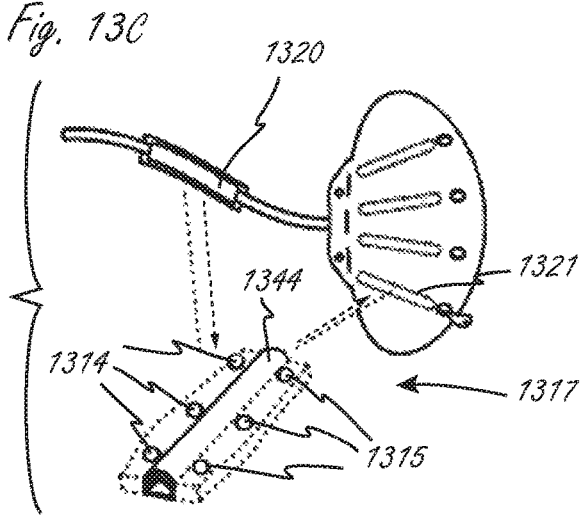
FIGS. 13C-13F illustrate additional embodiments of variable fluid resistor devices configured in accordance with the present technology.

In some FIG. 13C illustrates another embodiment of an inflow mounted variable resistor 1320 in accordance with the present technology. In this embodiment, multiple actuation elements 618 can be arrayed serially along a length of control lumen 636 (FIG. 13A). As the expansion portion 1314 of each target actuation element 1318 is actuated, the length of the restricted area is increased thereby increasing the fluid resistance linearly. Likewise, actuating shrinkage portion(s) 1315 of target actuation element(s) 1318 can decease fluid resistance. As shown in FIG. 13C, such fluid controls can be incorporated into a shunt plate 1303, inflow tube 1305, an outflow mounted variable resistor 1321, and/or the outflow tube (not shown).

Figure 13D:
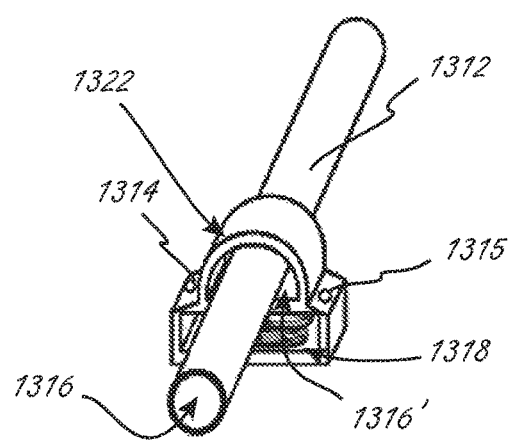

FIG. 13D illustrates a variable fluid resistor configured in accordance with still another embodiment of the present technology. The embodiment shown in FIG. 13D can include a number of features similar to those of the variable fluid resistors described above with reference to FIGS. 13A and 13B. In this embodiment, however, the elastomeric tube 1312 comprises a single fluid flow-through lumen 1316, while an actuation assembly 1322 positioned along the elastomeric tube 1312 comprises a dual-lumen arrangement similar to that described above. In particular, the actuation assembly 1322 comprises a first lumen 1316' having a predetermined cross-sectional shape (e.g., a "D" shaped lumen). The elastomeric tube 1312 is positioned within and extends through the first lumen 1316' of the actuation assembly 1322. The actuation assembly 1322 further comprises a second lumen or a control lumen 1336' adjacent the first lumen 1316'. The control lumen 1336' contains one or more actuation elements 1318 similar to the actuation elements described previously. In this embodiment, for example, the actuation element 1318 is composed of SMM and includes a first or expansion portion 1314 and a second or shrinkage portion 1315.

Selectively heating the expansion portion 1314 can cause the actuation element 1318 to expand. Like the arrangement described above with reference to FIGS. 13A and 13B, such expansion decreases the cross-sectional dimension of the elastomeric tube 1312 by driving the elastomeric tube 1312 away from the control lumen 1336' and toward fixed inner walls of the first lumen 1316'. By decreasing the cross-sectional dimension of the elastomeric tube 1312, fluid resistance through the tube 1312 is accordingly increased. The fluid resistance through elastomeric tube 1312 can be further decreased by additional heating of the expansion portion 1314, or the elastomeric tube 1312 can be returned to a lower resistance state via heating of the shrinkage portion 1315 of actuation element 1318. Although only a single actuation assembly 1322 is shown, it will be appreciated that in further embodiments multiple actuation assemblies 1322 can be positioned along a length of elastomeric tube 1312.

Figure 13E:
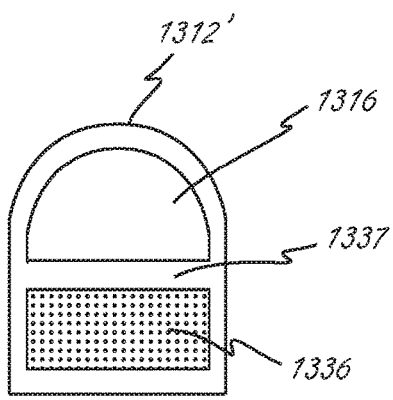
Figure 13F:
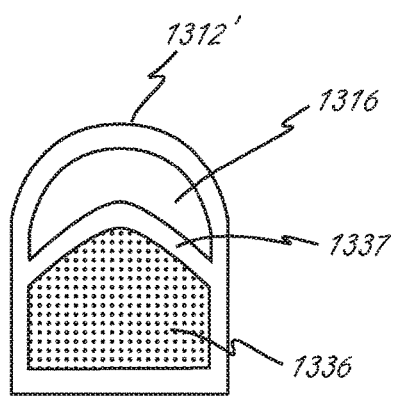

FIGS. 13E and 13F are partially schematic, cross-sectional views of a fluid resistor comprising a dual lumen elastomeric tube 1312' configured in accordance with yet another embodiment of the present technology. The fluid resistor in the embodiment illustrated in FIGS. 13E and 13F operates using a similar principle to that described above with reference to FIGS. 13A and 13B. For example, FIG. 13E illustrates the elastomeric tube 1312' in an initial or low-resistance state before modulation. The elastomeric tube 1312' comprises a first lumen or a fluid flow-through lumen 1316' having an initial cross-sectional shape (e.g., a "D" shaped lumen). The elastomeric tube 1312' further comprises a second lumen or a control lumen 1336' adjacent the first lumen 1316. The control lumen 1336' is filled with a control fluid. Referring next to FIG. 13F, when a volume of control fluid is increased, the cross-sectional dimension of the flow-through lumen 1316 is decreased as an elastomeric diaphragm 1337 expands into the flow-through lumen 1316', thereby increasing fluid resistance and decreasing flow through the lumen 1316'. Likewise, when control fluid is removed from the control lumen 1336', the elastomeric diaphragm 1337 retracts and the cross-sectional dimension of the flow-through channel 1316' is increased, thereby reducing fluid resistance and increasing outflow through the lumen 1316'. Control fluid can be removed or added to the control lumen 1336', for example, using a syringe. In some embodiments, one or more reservoirs (not shown) may be fluidly interfaced with the control lumen 1336' and fluid volume of the control lumen 1336' can be adjusted by adding or removing fluid from the reservoir(s). Further, it will be appreciated that in some embodiments fluid control systems configured in accordance with the present technology may comprise multiple fluid control sealed lumens serially distributed along the length of the control system.

Figure 14A:
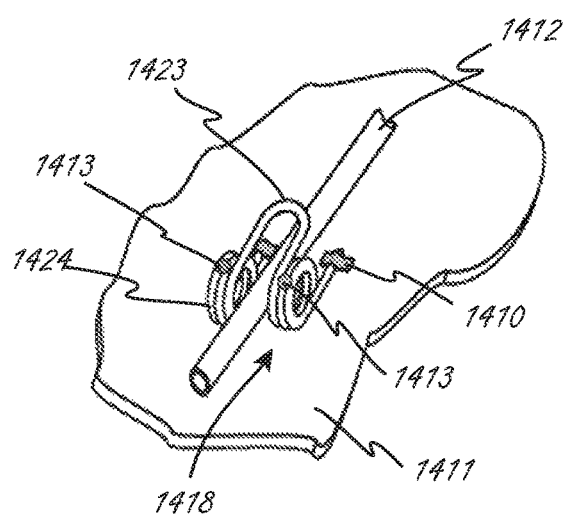
FIGS. 14A and 14B illustrate a fluid control element including variable fluid resistors composed of shape memory materials in accordance with additional embodiments of the present technology.
Figure 14B:
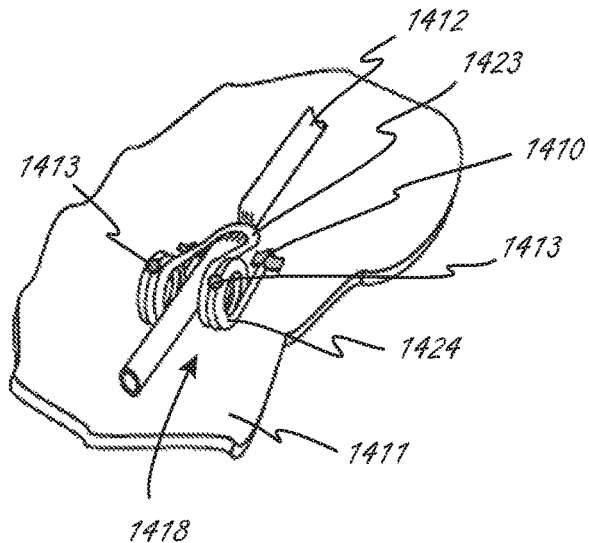

FIGS. 14A and 14B illustrate yet another embodiment of a SMM-based actuator 1418 configured in accordance with the present technology and adapted for use in an adjustable flow glaucoma shunt. In this embodiment, the actuator 1418 comprises one or more coils 1424 arranged about a periphery of clamping arm 1423. The coil(s) 1424 and clamping arm 1423 may both be composed of SMM. Anchors 1410 are positioned to fixedly hold the actuator 1418 in position on base 1411 such that the clamping arm 1423 is pressed against elastomeric flow-through tube 1412. The elastomeric flow-through tube 1412 can have a stiffness that maintains the outer coils 1424 in a state comparable to the mounted state for the ribbon/wire actuators 1318 described above with reference to FIGS. 12A-13B.

In operation, sections of the coil(s) 1424 can be selectively actuated to adjust the clamping pressure of the clamping arm 1423 against flow-through tube 1412, and thereby the fluid resistance. Referring to FIG. 14B, for example, coils 1424 on one side (e.g., the right side) of clamping arm 1423 can be heated via laser energy applied at target site 1413. Such heating actuates the selected coils 1424 and causes them to coil more tightly, thereby actuating the clamping arm 1423 to increase pressure and increase resistance on the flow-through tube 1412. Actuation of the coils 1424 on the other side of the clamping arm 1423 (the left side coils) relaxes the clamping arm 1423 and thereby decreases pressure and resistance on the flow-through tube 1412.

In alternate embodiments, the actuator 1418 can be set in a rest or initial position such that the clamping arm 1423 completely occludes the flow-through 1412 and the coils 1424 can be selectively adjusted to increase or decrease the tension of the clamping arm 1423 against the base 1411. The base 1411 accordingly acts as an anvil as the clamping arm 1423 drives the flow-through tube 1412 against it during operation. In some embodiments, such an arrangement may be used to operate an adjustable opening pressure valve (not shown), which is set to selectively control the desired control Intraocular Pressure (IOP). In other embodiments, however, the actuator 1418 may have a different arrangement and/or include different features.

FIGS. 15A-15C illustrate an adjustable glaucoma shunt 1500 configured in accordance with another embodiment of the present technology and include fluid resistor elements such as those described above with reference to FIGS. 14A and 14B. FIG. 15A, for example, is an exploded view of the shunt 1500, and FIG. 15B is a top view of the assembled shunt 800. Referring to FIGS. 15A and 15B together, the shunt 1500 comprises an elastomeric flow-through tube 1512 carried by and operably coupled with control assembly 1519. The flow-through tube 1512 comprises an inflow region or inflow portion 1505 at one end of the flow-through tube 1512, and an outflow assembly 1527 including one or more outflow ports 1502 at or near an opposite end of the flow-through tube 1512.

The shunt 1500 also includes an actuator 1518 carried by and operably coupled to control assembly 1519. The actuator 1518 can be similar to the actuator 1418 described above with reference to FIGS. 14A and 14B. In the illustrated embodiment, for example, actuator 1518 includes a clamping arm 1523 operably coupled to and positioned between a plurality of coils 1524. The coils 1524 (like the coils 1424 described above) can be composed of SMM and adapted to selectively modulate the flow-through tube 1512 to increase/decrease pressure therethrough as described previously.

In the illustrated embodiment, the shunt 1500 includes a pressure port 1528 and corresponding pressure transducer 1529 configured to be positioned within a pressure transducer housing 1530 on the control assembly 1519. The pressure port 1528/pressure transducer 1529 are configured to provide pressure information to a clinician/operator during operation of the shunt 1500. In other embodiments, the pressure port and/or pressure transducer 1529 may have a different arrangement relative to each other and the other components of the shunt 1500. Further, the pressure port 1528/pressure transducer 1529 are optional components that may not be included in some embodiments. In some embodiments, the shunt 1500 may also optionally include a differential port 1526 in the control assembly 1519.

The shunt 1500 can further include a plate 1503 configured to be positioned over at least a portion of the control assembly 1518, flow-through tube 1512, and actuator 1518. The plate 1503 can include a window 1531 such that when the shunt 1500 is assembled (as shown in FIG. 15B), the window 1531 provides access to the actuator 1518 and other components carried by the control assembly 1519.

FIG. 15C illustrates an implant tool 1534 configured to deliver and position shunt 1500 within an eye capsule of a patient (not shown) in accordance with an embodiment of the present technology. The implant tool 1534 can include, for example, a guide needle 1532 configured to carry the shunt 1500 for delivery, and a guide needle release 1533 that an operator can actuate to release the shunt 1500 once at a desired position/orientation within the patient. In other embodiments, however, the implant tool 1534 may have a different configuration and/or the shunt 1500 may be delivered using other suitable devices/techniques.

Figure 16A:
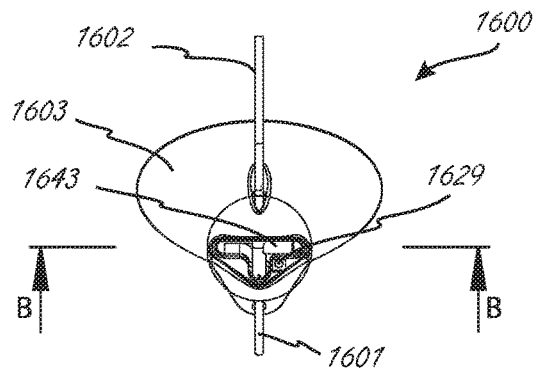
FIGS. 16A-16E illustrate an adjustable flow glaucoma shunt configured in accordance with still another embodiment of the present technology.

FIGS. 16A-16E illustrate various features of an adjustable glaucoma shunt 1600 configured in accordance with yet another embodiment of the present technology. The shunt 1600 can include a number of features similar to the shunt 1500 described above with reference to FIGS. 15A-15C. For example, as best seen in FIG. 16A, the shunt 1600 comprises a flow-through tube 1612 having an inflow port or inflow region 1601 at one end, and an outflow port 1602 at an opposite end of the flow-through tube 1612. The shunt 1600 further comprises a control assembly 1619 configured to modulate flow through the flow-through tube 1612. The flow-through tube 1612, control assembly 1619, and a number of other components of the shunt are carried by plate 1603.

Figure 16B:
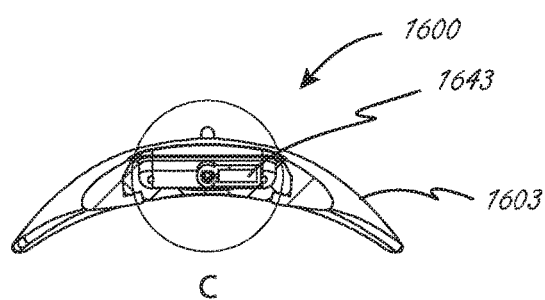
Figure 16C:
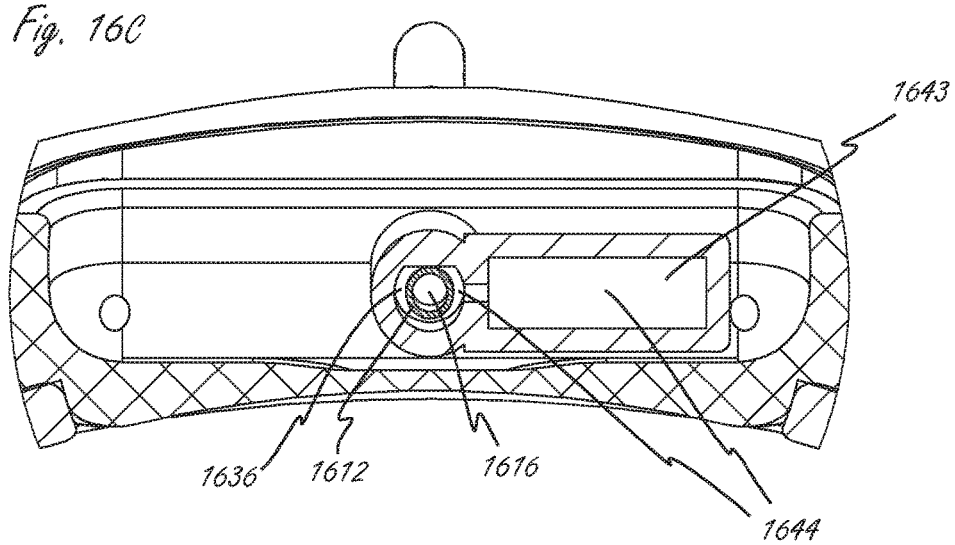
Figure 16D:
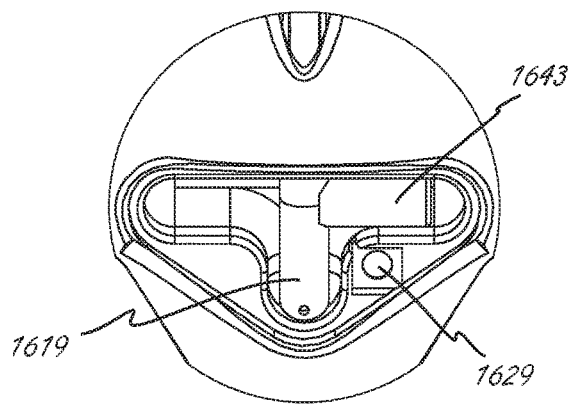

The shunt 1600 differs from the shunt 1500, however, in that the shunt 1600 includes a different system for modulating fluid flow along the flow-through tube 1612. In particular, rather than the actuator 1518 including the clamping arm 1523/coils 1524 described previously, the shunt 1600 in the present embodiment comprises an arrangement similar to that described above with reference to FIGS. 13E and 13F. Referring to FIGS. 16B-16D, for example, the control assembly 1629 of shunt 1600 comprises a control fluid 1644 contained within a control fluid chamber 1636 comprising an annular region around a thin walled tubular flow-through channel of tube 1612. The control fluid chamber 1636 is fluidly isolated from the flow-through channel. A reservoir 1643 is interfaced with and in fluid communication with the control fluid chamber. The reservoir 1643 is configured to provide a larger target for conveniently injecting or removing control fluid 1636 from the system. In operation, control fluid 1644 may be added/removed from the control fluid chamber 1636 to increase/decrease a fluid cross-sectional dimension of an aqueous flow path 1616 through flow-through channel 1612, thereby decreasing/increasing the corresponding fluid flow therethrough.

Figure 16E:
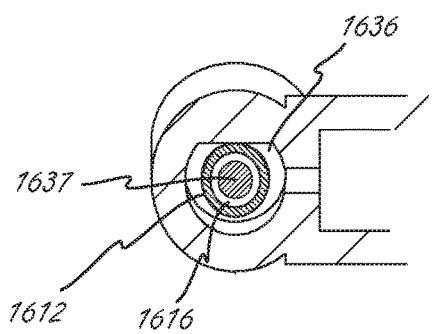

In some embodiments, a solid core may optionally be introduced into flow path 1616 to initially reduce the fluid cross-sectional dimension even further and thereby make the flow path more sensitive to small changes in the diameter of flow-through channel 1612. In FIG. 16E, for example, optional solid core pin or element 1637 has been introduced into the flow-through channel 1612 and flow path 1616 now has an annular cross-sectional profile.

In the illustrated embodiment, the shunt 1600 further comprises a pressure transducer 1629. The pressure transducer 1629 is an optional component that may not be included in some embodiments. Further, it will be appreciated that shunt 1600 may include features other than those described herein and/or the features of shunt 1600 may have a different arrangement relative to each other.

In many of the embodiments described herein, the actuators or fluid resistors are configured to compress or "pinch" the drainage tube during operation. In this way, the actuators/fluid resistors can incrementally or continuously change the flow resistance through the drainage tube to selectively regulate pressure/flow. The actuators and fluid resistors configured in accordance with the present technology can accordingly adjust the level of resistance or compression between a number of different positions, and accommodate a multitude of variables (e.g., IOP, aqueous production rate, native aqueous outflow resistance, and/or native aqueous outflow rate) to precisely regulate flow rate through the drainage tube.

The disclosed actuators and fluid resistors can all be operated using non-invasive energy. This feature allows such devices to be implanted in the patient and then modified/adjusted over time without further invasive surgeries or procedures for the patient. Further, because the devices disclosed herein may be actuated via non-invasive energy, such devices do not require any additional power to maintain a desired orientation or position. Rather, the actuators/fluid resistors disclosed herein can maintain a desired position/orientation without power. This can significantly increase the usable lifetime of such devices and enable such devices to be effective long after the initial implantation procedure.

Examples

Several aspects of the present technology are set forth in the following examples.

1. An adjustable flow shunt for treating glaucoma in a human patient, the shunt comprising:
   an elongated outflow drainage tube having a proximal inflow region and a distal outflow region; and
   an inflow control assembly at the proximal inflow region, wherein the inflow control assembly comprises—
      a control element sized and shaped to slidably engage the proximal inflow region; and
      a spring element operably coupled between the control element and an anchor element engaged with the proximal inflow region;
   wherein the proximal inflow region comprises one or more apertures defining a fluid inlet area positioned to allow fluid to flow therethrough and into the outflow drainage tube,
   wherein the spring element is configured to be activated by a non-invasive energy and, upon activation, slidably actuate the control element along the proximal inflow region such that (a) the one or more apertures are accessible and have a first fluid flow cross-section or (b) the one or more apertures are at least partially covered by the control element and have a second fluid-flow cross-section less than the first fluid flow cross-section.

2. The adjustable flow shunt of example 1 wherein the proximal inflow region comprises a core element operably coupled to and extending from a proximal end of the outflow drainage tube, and wherein the one or more apertures extend through a sidewall of the core element to define the fluid inlet area.

3. The adjustable flow shunt of example 2 wherein the core element is composed of a different material than the outflow drainage tube.

4. The adjustable flow shunt of example 2 wherein the core element is composed of a first material having a first rigidity, and wherein the outflow drainage tube is composed of a second material having a second rigidity less than the first rigidity.

5. The adjustable flow shunt of example 2 wherein the core element is composed of polyether ether ketone (PEEK), acrylic, polycarbonate, metal, ceramic, quartz, and/or sapphire.

6. The adjustable flow shunt of any one of examples 1-5 wherein the elongated outflow drainage tube is composed of silicone and/or urethane.

7. The adjustable flow shunt of any one of examples 1-6 wherein the spring element is composed of a shape memory material.

8. The adjustable flow shunt of any one of examples 1-6 wherein the spring element is composed of nitinol.

9. The adjustable flow shunt of any one of examples 1-8 wherein the inflow control assembly is configured for placement within an anterior chamber in a region outside of the optical field of view of the eye.

10. The adjustable flow shunt of example 9 wherein the outflow drainage tube is sized and shaped to traverse a region between the anterior chamber to a region in a suprachoroidal location of the eye.

11. The adjustable flow shunt of example 9 wherein the outflow drainage tube is sized and shaped to traverse a region between the anterior chamber to a region in a subconjunctival location of the eye.

12. The adjustable flow shunt of any one of examples 1-11 wherein the one or more apertures comprises a single elongated slot extending axially along the proximal inflow region.

13. The adjustable flow shunt of any one of examples 1-11 wherein the one or more apertures comprises a plurality of apertures extending radially about the proximal inflow region.

14. The adjustable flow shunt of any one of examples 1-11 wherein the one or more apertures comprises a plurality of apertures extending helically about the proximal inflow region.

15. The adjustable flow shunt of any one of examples 1-14 wherein the spring element is configured to be activated via laser energy.

16. The adjustable flow shunt of any one of examples 1-15 wherein the spring element comprises a first spring and the anchor comprises a first anchor, and wherein the first spring and first anchor are positioned on a first side of the control element, and wherein the inflow control assembly further comprises:
    a second spring and a corresponding second anchor on a second, opposite side of the control element;
    wherein the first and second spring elements are configured to be selectivity activated by non-invasive energy and, upon activation, slidably move the control element along the proximal inflow region in a first direction or a second direction, respectively, such that (a) the one or more apertures have the first fluid flow cross-section, or (b) the one or more apertures are at least partially covered by the control element and have the second fluid-flow cross-section less than the first fluid flow cross-section.

17. The adjustable flow shunt of example 16 wherein the first and second spring elements are configured such that, upon activation, the control element slidably moves the control element along the proximal inflow region such that the one or more apertures are fully covered and inaccessible.

18. The adjustable flow shunt of any one of examples 1-15 wherein the spring element and corresponding anchor element are positioned on a proximal end of the control element between the control element and the outflow drainage tube.

19. The adjustable flow shunt of any one of examples 1-15 wherein the spring element comprises one or more coil springs extending about the proximal inflow region.

20. The adjustable flow shunt of any one of examples 1-15 wherein the spring element comprises one or more elongated bow springs extending between the control element and the anchor element.

21. An adjustable flow shunt assembly for treatment of glaucoma, the shunt assembly comprising:
    an elongated drainage tube having a proximal portion and a distal portion, wherein the proximal portion includes an inflow port configured to be in fluid communication with a fluid chamber in an eye of the patient;
    a variable resistor assembly configured to selectively control flow of fluid into the inflow port, wherein the variable resistor assembly comprises—
    a base portion;
    an aperture plate carried by the base portion, wherein the aperture plate comprises a plurality of first apertures extending therethrough;
    a standoff plate carried by and extending away from the aperture plate, wherein the standoff plate comprises a plurality of second apertures extending therethrough, and wherein the second apertures are aligned with corresponding first apertures of the aperture plate; and
    a membrane disposed on a carried by the standoff plate, wherein the membrane is positioned to sealably cover an open end of each of the second apertures;
    wherein, during operation, a portion of the membrane over one or more second apertures of the standoff plate is configured to be selectively targeted and removed via non-invasive energy, thereby creating a fluid path from the site of fluid in the patient through the accessible open ends of the targeted second apertures, the corresponding first apertures, and into the drainage tube.

22. The adjustable flow shunt assembly of example 21 wherein:
    the first apertures have a first cross-sectional dimension; and
    the second apertures have a second cross-sectional dimension greater than the first cross-sectional dimension.

23. The adjustable flow shunt assembly of example 21 wherein the first apertures have identical cross-sectional dimensions.

24. The adjustable flow shunt assembly of any one of examples 21-23 wherein the standoff plate is composed, at least in part, of a hydrophobic material configured to be at least partially melted via non-invasive energy.

25. The adjustable flow shunt assembly of any one of examples 21-23 wherein the standoff plate is composed, at least in part, of a wax material configured to be at least partially melted via non-invasive energy.

26. The adjustable flow shunt assembly of any one of examples 21-23 wherein the base portion, aperture plate, and standoff plate of the variable resistor assembly are separate, discrete components operably coupled together.

27. The adjustable flow shunt assembly of any one of examples 21-23 wherein the standoff plate and membrane are fabricated as a single, unitary component composed of the same material.

28. The adjustable flow shunt assembly of any one of examples 21-23 wherein the aperture plate and standoff plate are fabricated as a single, unitary component composed of the same material.

29. The adjustable flow shunt assembly of any one of examples 21-28 wherein:
    the membrane further comprises a plurality of target indicia aligned with and corresponding with individual second apertures; and
    during operation, the non-invasive energy is delivered to corresponding target indicia of the membrane to selectively remove membrane material at the targeted location.

30. An adjustable flow shunt for treatment of glaucoma in a human patient, the adjustable flow shunt comprising:
- an elongated outflow tube having (a) a proximal inflow portion configured for placement within an anterior chamber in a region outside of an optical field of view of an eye of the patient, and (b) a distal outflow portion at a different location of the eye; and
- an actuator positioned along the outflow tube between the inflow portion and the outflow portion, wherein the actuator is transformable between an open position that allows fluid to flow through the outflow tube and resistance positions that partially obstruct fluid flow through the outflow tube,
- wherein during operation, the actuator is movable between positions in response to non-invasive energy.

31. The adjustable flow shunt of example 30 wherein the actuator is configured to partially obstruct fluid flow through the outflow tube in the resistance positions by engaging the outflow tube and changing a diameter and/or a cross-sectional shape of the outflow tube.

32. The adjustable flow shunt of example 30 or example 31 wherein the actuator is movable between positions in response to laser energy.

33. The adjustable flow shunt of example 30 wherein:
- the outflow tube comprises a dual lumen tube having a first lumen for carrying fluid therethrough and a second lumen adjacent to the first lumen and separated by the first lumen by a diaphragm;
- the actuator is positioned within the second lumen, and wherein the actuator comprises one or more actuation elements configured to transform between and expanded state and an initial state in response to the non-invasive energy,
- in the expanded state, actuation elements engage and push the diaphragm toward the first lumen and decrease a cross-sectional dimension thereof.

34. The adjustable flow shunt of any one of examples 30-33 wherein the actuator is configured to hold the open position or one of the resistance positions without power.

35. An adjustable flow shunt, comprising:
- an elongated outflow tube having a proximal inflow portion configured for placement at a first location within an eye of the patient, and a distal outflow portion at a second location of the eye spaced apart from the first location,
- wherein the outflow tube comprises a dual lumen tube having a first lumen for carrying fluid therethrough and a second lumen adjacent to the first lumen and fluidly isolated from the first lumen; and
- a control fluid disposed within the second lumen,
- and wherein, during operation—
  - increasing a volume of control fluid within the second lumen decreases a cross-sectional dimension of the first lumen, thereby partially obstructing fluid flow through the first lumen, and
  - decreasing a volume of control fluid within the second lumen increases a cross-sectional dimension of the first lumen, thereby increasing fluid flow through the first lumen.

36. The adjustable flow shunt of example 35 wherein the elongated outflow tube comprises an elastomeric tube.

37. The adjustable flow shunt of example 35 or example 36, further comprising a reservoir in fluid communication with the second lumen, and wherein the volume of control fluid within the second lumen is changed by transferring control fluid to and/or from the reservoir.

38. The adjustable flow shunt of any one of examples 35-37 wherein the volume of control fluid within the second lumen is changed by transferring control fluid to and/or from the second lumen via a syringe.

39. The adjustable flow shunt of any one of examples 35-38 wherein the first lumen is separated from the second lumen by a diaphragm, and wherein:
- increasing a volume of control fluid within the second lumen moves the diaphragm toward the first lumen and decreases a cross-sectional dimension thereof; and
- decreasing a volume of control fluid within the second lumen moves the diaphragm away from the first lumen and increases a cross-sectional dimension thereof.

40. A shunt for treatment of glaucoma in a human patient, the shunt comprising: an elongated outflow drainage tube having a proximal inflow region and a distal outflow region;
- an inflow control assembly at the proximal inflow region; and
- a transition region along the outflow tube between the inflow region and the outflow region, wherein, during operation, the transition region is transformable between a first generally linear delivery shape and a second shape different than the first shape to anchor the shunt at a desired location of the eye.

41. The shunt of example 40 wherein the outflow drainage tube is configured to be delivered via guidewire, and wherein the transition region is configured to transform between the first delivery shape and the second shape upon removal of the guidewire.

42. The shunt of example 40 or example 41 wherein the transition region is configured to transform between the first delivery shape and the second shape upon application of non-invasive energy to one or more selected areas of the transition region.

43. The shunt of example 40 or example 41 wherein the transition region is configured to transform between the first delivery shape and the second shape in response to application of non-invasive laser energy to one or more selected areas of the transition region.

44. The shunt of any one of examples 40-43 wherein the second shape comprises a generally "L" shaped configuration.

CONCLUSION

The above detailed description of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, any of the features of the variable flow shunts described herein may be combined with any of the features of the other variable flow shunts described herein and vice versa. Moreover, although steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions associated with variable flow shunts have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. An adjustable flow shunt for treating glaucoma in a human patient, the shunt comprising:
    an elongated outflow drainage tube having a proximal inflow region and a distal outflow region; and
    an inflow control assembly at the proximal inflow region, wherein the inflow control assembly comprises—
        a control element sized and shaped to slidably engage the proximal inflow region; and
        a shape memory actuation element operably coupled between the control element and an anchor element engaged with the proximal inflow region;
    wherein the proximal inflow region comprises one or more apertures defining a fluid inlet area positioned to allow fluid to flow therethrough and into the outflow drainage tube,
    wherein the shape memory actuation element is configured to be selectively activated by a non-invasive energy and, upon activation, slidably actuate the control element along the proximal inflow region such that (a) the one or more apertures are accessible and have a first fluid flow cross-section or (b) the one or more apertures are at least partially covered by the control element and have a second fluid-flow cross-section less than the first fluid flow cross-section.

2. The adjustable flow shunt of claim 1 wherein the proximal inflow region comprises a core element operably coupled to and extending from a proximal end of the outflow drainage tube, and wherein the one or more apertures extend through a sidewall of the core element to define the fluid inlet area.

3. The adjustable flow shunt of claim 2 wherein the core element is composed of a different material than the outflow drainage tube.

4. The adjustable flow shunt of claim 2 wherein the core element is composed of a first material having a first rigidity, and wherein the outflow drainage tube is composed of a second material having a second rigidity less than the first rigidity.

5. The adjustable flow shunt of claim 2 wherein the core element is composed of polyether ether ketone (PEEK), acrylic, polycarbonate, metal, ceramic, quartz, and/or sapphire.

6. The adjustable flow shunt of claim 1 wherein the elongated outflow drainage tube is composed of silicone and/or urethane.

7. The adjustable flow shunt of claim 1 wherein the shape memory actuation element is composed of nitinol.

8. The adjustable flow shunt of claim 1 wherein the inflow control assembly is configured for placement within an anterior chamber in a region outside of the optical field of view of the eye.

9. The adjustable flow shunt of claim 8 wherein the outflow drainage tube is sized and shaped to traverse a region between the anterior chamber to a region in a suprachoroidal location of the eye.

10. The adjustable flow shunt of claim 8 wherein the outflow drainage tube is sized and shaped to traverse a region between the anterior chamber to a region in a subconjunctival location of the eye.

11. The adjustable flow shunt of claim 1 wherein the one or more apertures comprises a single elongated slot extending axially along the proximal inflow region.

12. The adjustable flow shunt of claim 1 wherein the one or more apertures comprises a plurality of apertures extending radially about the proximal inflow region.

13. The adjustable flow shunt of claim 1 wherein the one or more apertures comprises a plurality of apertures extending helically about the proximal inflow region.

14. The adjustable flow shunt of claim 1 wherein the shape memory actuation element is configured to be activated via laser energy.

15. The adjustable flow shunt of claim 1 wherein the shape memory actuation element comprises a first shape memory actuation element and the anchor comprises a first anchor, and wherein the first shape memory actuation element and first anchor are positioned on a first side of the control element, and wherein the inflow control assembly further comprises:
    a second shape memory actuation element and a corresponding second anchor on a second, opposite side of the control element;
    wherein the first and second shape memory actuation elements are configured to be selectivity activated by non-invasive energy and, upon activation, slidably move the control element along the proximal inflow region in a first direction or a second direction, respectively, such that (a) the one or more apertures have the first fluid flow cross-section, or (b) the one or more apertures are at least partially covered by the control element and have the second fluid-flow cross-section less than the first fluid flow cross-section.

16. The adjustable flow shunt of claim 15 wherein the first and second shape memory actuation elements are configured such that, upon activation, the control element slidably moves the control element along the proximal inflow region such that the one or more apertures are fully covered and inaccessible.

17. The adjustable flow shunt of claim 1 wherein the shape memory actuation element and corresponding anchor element are positioned on a proximal end of the control element between the control element and the outflow drainage tube.

18. The adjustable flow shunt of claim 1 wherein the shape memory actuation element is configured to coil more tightly about the proximal inflow region upon activation.

19. The adjustable flow shunt of claim 1 wherein the shape memory actuation element is configured to bow outwardly away from the elongated outflow drainage tube upon activation.

20. An adjustable flow shunt, comprising:
an elongated drainage element having an opening in fluid communication with an interior of the elongated drainage element; and
a control assembly configured to control the flow of fluid through the elongated drainage element, wherein the control assembly comprises—
 a control element sized and shaped to slidably engage the elongated drainage element; and
 a shape memory actuation element operably coupled between the control element and an anchor element engaged with the elongated drainage element;
wherein the shape memory actuation element is configured to be selectively activated by a non-invasive energy and, upon activation, slidably actuate the control element along the elongated drainage element to (a) make the opening more accessible, or (b) make the opening less accessible.

* * * * *